(12) United States Patent
Yilmaz et al.

(10) Patent No.: US 7,919,316 B2
(45) Date of Patent: Apr. 5, 2011

(54) HEMATOPOIETIC STEM CELL IDENTIFICATION AND ISOLATION

(75) Inventors: Omer H. Yilmaz, Ann Arbor, MI (US); Mark J. Kiel, Ann Arbor, MI (US); Sean Morrison, Ann Arbor, MI (US); Toshihide Iwashita, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 52 days.

(21) Appl. No.: 12/389,143

(22) Filed: Feb. 19, 2009

(65) Prior Publication Data

US 2009/0227019 A1    Sep. 10, 2009

Related U.S. Application Data

(63) Continuation of application No. 10/950,784, filed on Sep. 27, 2004, now Pat. No. 7,510,877.

(60) Provisional application No. 60/506,111, filed on Sep. 26, 2003.

(51) Int. Cl.
*C12N 5/0789* (2010.01)
*C12N 5/074* (2010.01)

(52) U.S. Cl. .................. 435/372; 435/370; 435/325

(58) Field of Classification Search .................. 435/325, 435/370, 372
See application file for complete search history.

(56) References Cited

U.S. PATENT DOCUMENTS

| | | | |
|---|---|---|---|
| 5,061,620 | A | 10/1991 | Tsukamoto |
| 5,646,001 | A | 7/1997 | Terstappen |
| 5,840,502 | A | 11/1998 | Van Vlasselaer |
| 6,353,150 | B1 | 3/2002 | Dick |

FOREIGN PATENT DOCUMENTS

| | | |
|---|---|---|
| JP | 6-269293 | 9/1994 |
| JP | 10-94390 | 4/1998 |
| JP | 10-136978 | 5/1998 |
| WO | WO 98/21313 | 5/1998 |
| WO | WO/00/14203 A1 * | 3/2000 |

OTHER PUBLICATIONS

Natori et al. 2000 Method for Preparing a Cell Fraction Containing Hematopoietic Stem Cells. English Translation (human) for WO/2000/14203. p. 1-32.*
Adult Stem Cells. 2002. Stem Cells and Future of Regenerative Medicine. Chapter Two. p. 19.*
Kiel et al. 2005. SLAM Family Receptors Distinguish Hematopoietic Stem and Progenitor Cells and Reveal Endothelial Niches for Stem Cells. Cell. 121:1109-1121.*
Morrison S.J. et al. The biology of hematopoietic stem cells. Annu Rev Cell Dev Biol. 1995;11:35-71.
Domen et al. Self-renewal, differentiation or death: regulation and manipulation of hematopoietic stem cell fate. Mol Med Today. May 1999;5(5):201-8.
Uchida & Weissman. Searching for hematopoietic stem cells: evidence that Thy-1.110 Lin-Sca-1 + cells are the only stem cells in C57BUKa-Thy-1.1 bone marrow. J Exp Med. Jan. 1, 1992; 175(1):175-84.
Morrison & Weissman. The long-term repopulating subset of hematopoietic stem cells is deterministic and isolatable by phenotype. Immunity. Nov. 1994;1(8):661-73.
Morrison et al. Identification of a lineage of multipotent hematopoietic progenitors. Development. May 1997;124(1 0):1 929-39.
Wagers et al. Little evidence for developmental plasticity of adult hematopoietic stem cells. Science. Sep. 27, 2002;297(5590):2256-9.
Osawa et al. Long-term lymphohematopoietic reconstitution by a single CD34-low/negative hematopoietic stem cell. Science. Jul. 12, 1996;273(5272):242-5.
Wang et al. CD150 is a member of a family of genes that encode glycoproteins on the surface of hematopoietic cells. Immunogenetics. Jul. 2001;53(5):382-94.
Howie et al. Molecular dissection of the signaling and costimulatory functions of CD150 (SLAM): CD150/SAP binding and CD150-mediated costimulation. Blood. Feb. 1, 2002;99(3):957-65.
Howie et al. The role of SAP in murine CD150 (SLAM)-mediated T-cell proliferation and interferon gamma production. Blood. Oct. 15, 2002;100(8):2899-907.
Castro et al. Molecular and functional characterization of mouse signaling lymphocytic activation molecule (SLAM): differential expression and responsiveness in Th1 and Th2 cells. J Immunol. Dec. 1, 1999;163(11):5660-70.
Sidorenko et al. The dual-function CD150 receptor subfamily: the viral attraction. Nat Immunol. Jan. 2003;4(1):19-24.
Yanagi et al. Measles virus receptor SLAM (CD150). Virology. Aug. 1, 2002;299(2):155-61.
Chan et al. SAP couples Fyn to SLAM immune receptors. Nat Cell Biol. Feb. 2003;5(2): 155-60.
Morra et al. Characterization of SH2D1A missense mutations identified in X-linked lymphoproliferative disease patients. J Bioi Chem. Sep. 28, 2001;276(39):36809.
Wiesmann et al. Expression of C027 on murine hematopoietic stem and progenitor cells. Immunity. Feb. 2000;12 (2):193-9.
Christensen et al. Flk-2 is a marker in hematopoietic stem cell differentiation: a simple method to isolate long-term stem cells. Proc Natl Acad Sci USA. Dec. 4, 2001;98(25):14541-6.
Schneider-Schaulies et al. Measles virus induced immunosuppression: targets and effector mechanisms. Curr Mol Med. May 2001; 1(2): 163-81.
Morra et al. X-linked lymphoproliferative disease: a progressive immunodeficiency. Annu Rev Immunol. 2001 ;19:657-82.

(Continued)

*Primary Examiner* — Taeyoon Kim
(74) *Attorney, Agent, or Firm* — Casimir Jones, S.C.

(57) ABSTRACT

The present invention relates to methods of identifying, collecting and isolating hematopoietic stem cells (HSCs) and compositions of purified HSCs. Specifically, the present invention provides methods of isolating and purifying $CD150^+$ HSCs, $CD48^-$ HSCs, and $CD244^-$ HSCs. The present invention also relates to purified cell samples with enriched $CD150^+$ HSCs, $CD48^-$ HSCs, and $CD244^-$ HSCs populations, as well as methods of treating subjects with such compositions.

12 Claims, 6 Drawing Sheets

OTHER PUBLICATIONS

Nelson et al. X-linked lymphoproliferative syndrome. Clin Exp Immunol. Dec. 2000;122(3):291-5.

Ando, K. Human CD34– hematopoietic stem cells: basic features and clinical relevance. Int J Hematol. May 2002;75 (4):370-5.

Bhatia et al. A newly discovered class of human hematopoietic cells with SCID-repopulating activity. Nat Med. Sep. 1998;4(9):1038-45.

Donnelly et al. Hematopoietic stem cells can be CD34+ or CD34–. Leuk Lymphoma. Jan. 2001;40(3-4):221-34.

Engelhardt et al. CD34(+) or CD34(–): which is the more primitive? Leukemia. Sep. 2002;16(9):1603-8.

Guo et al. CD34– hematopoietic stem cells: current concepts and controversies. Stem Cells. 2003;21 (1): 15-20.

Nakauchi, H. Hematopoietic stem cells: are they CD34-positive or CD34- negative? Nat Med. Sep. 1998;4 (9):1009-10.

Ogawa M. Changing phenotypes of hematopoietic stem cells. Exp Hematol. Jan. 2002;30(1):3-6.

Iwashita et al. Hirschsprung disease is linked to defects in neural crest stem cell function. Science 2003; 301:972.

Romero et al. Differential expression of SAP and EAT-2-binding leukocyte cell-surface molecules CD84, CD150 (SLAM), CD229 (Ly9) and CD244 (284), Tissue Antigens 2004; 64, No. 2, 132-144.

Osawa et al. In vivo self-renewal of c-Kit+ Sca-1 + Lin low/– hemopoietic stem cells, J. Immunol. (1996), vol. 156, No. 9, pp. 3207-3214.

Christensen et al. Fl k-2 is a marker in hematopoietic stem cell differentiation: A simple method to isolate long-term stem cells. Proceedings of the National Academy of Sciences of the United States of America 2001; 98 No. 25, 14541-14546.

\* cited by examiner

HEMATOPOIETIC STEM CELL IDENTIFICATION AND ISOLATION

The present application is a Continuation of U.S. patent application Ser. No. 10/950,784, now allowed, which in turn claims priority to U.S. Provisional Application Ser. No. 60/506,111, filed Sep. 26, 2003, both of which are herein incorporated by reference in their entireties.

STATEMENT REGARDING FEDERALLY SPONSORED RESEARCH OR DEVELOPMENT

This invention was made with government support under grant number DAADI9-03-1-0168 from the U.S. Army Research Laboratory and the U.S. Army Research Office. The government has certain rights in the invention.

FIELD OF THE INVENTION

The present invention relates to methods of identifying, collecting and isolating hematopoietic stem cells (HSCs) and compositions of purified HSCs. Specifically, the present invention provides methods of isolating and collecting $CD150^+$ HSCs, $CD48^-$ HSCs, and $CD244^-$ HSCs. The present invention also relates to purified cell samples with enriched $CD150^+$ HSCs, $CD48^-$ HSCs, and $CD244^-$ HSCs populations, as well as methods of treating subjects with such compositions.

BACKGROUND OF THE INVENTION

Hematopoietic stem cells (HSCs) in the bone marrow are responsible for the production of mature blood cells throughout adult life. HSCs are identified by their ability to self-renew and undergo multilineage differentiation to form all major lineages of blood cells. HSCs can be transplanted into irradiated subjects, where they will engraft and give rise large numbers of diverse types of blood cells including myeloid, B, and T cells.

The state of the art for HSC purification relies on complex combinations of up to 12 markers, which target specific cell surface proteins, to isolate HSCs from bone marrow or other hematopoietic tissues by flow-cytometry. The highest enrichment of HSC activity yet reported describes combinations of markers, such those used to isolate Thy-1.1$^{lo}$Sca-1$^+$lineage$^-$Mac-1$^-$CD4$^-$-c-kit$^+$ cells (hereafter referred to as Mac-1$^-$CD4$^-$c-kit$^+$), from which one out of every five intravenously injected cells are able to home to bone marrow and engraft (see, e.g., Uchida et al., J Exp Med. 1992 Jan. 1; 175(1):175-84; Morrison et al., Immunity. 1994 November; 1(8):661-73; and Morrison et al., Development. 1997 May; 124(10):1929-39, all of which are herein incorporated by reference). HSCs are characterized by the ability to undergo long-term multi-lineage reconstitution (for extended periods of time and usually for the life of a subject, in the case of a murine subject, for more than 16 weeks to life), whereas other populations of hematopoietic progenitors only transiently form mature blood cells. For example, HSCs give rise to non-self-renewing multipotent progenitors (MPPs) that can be isolated as Thy-1.1$^{lo}$Sca-1$^+$Mac-1$^{lo}$CD4$^{lo}$ bone marrow cells (See, Morrison et al., 1994 and Morrison et al. 1997 supra). These cells give rise to myeloid B and T cells for less than 6 weeks after injection into irradiated mice, for example.

Highly purified HSCs are increasingly being used clinically, such as for autologous transplants into patients after high-dose chemotherapy. In this setting it is critical to isolate HSCs with the maximum degree of purity, to minimize contamination by immune effector cells (such as lymphocytes) or cancer cells. Since few markers or cell surface proteins have been identified that are highly specific to HSCs, it is not possible to identify or collect these cells based on simple combinations of one or two markers. As a result, it has only been possible to highly purify HSCs using complex combinations of many markers. These complex combinations of markers have not been practical to use clinically. As a result, simplified combinations of one or two markers (e.g., monoclonal antibodies that can identify $CD34^+$ or $CD34^+CD38^-$ cells) have often been used for the clinical isolation of HSCs, but these yield much lower levels of purity. Thus it would be desirable to identify new cell surface proteins, and/or markers corresponding thereto, that improve and simplify the purification of HSCs to facilitate their clinical use.

SUMMARY OF THE INVENTION

The present invention provides methods of identifying and collecting hematopoietic stem cells (HSCs) and compositions highly enriched for HSCs. In particular, the present invention provides methods of purifying HSCs (e.g. from a hematopoietic tissue sample) based on the presence or absence of SLAM family member proteins, and especially CD150, CD48, and CD244. In certain embodiments, the present invention provides methods of identifying and collecting $CD150^+$ HSCs, $CD150^+CD48^-$ HSCs, $CD150^+CD244^-$ HSCs, and $CD150^+CD48^-CD244^-$ HSCs from a cell sample, as well as purified samples having an increased level of $CD150^+$ HSCs, $CD150^+CD48^-$ HSCs, $CD150^+CD244^-$HSCs, and $CD150^+CD48^-CD244^-$ HSCs. The present invention also provides methods of treating subjects with such compositions.

In some embodiments, the present invention provides methods comprising a) providing a first sample comprising hematopoietic stem cells (HSCs) and b) purifying the first sample under conditions such that a purified sample is generated, wherein the purified sample comprises a higher percent of $CD150^+$ HSCs, $CD48^-$ HSCs, or $CD244^-$ HSCs than present in the first sample. In particular embodiments, the present invention provides compositions purified by the above method.

In certain embodiments, the present invention provides methods comprising: purifying cells from a first sample, based on the positive expression of CD150 protein or negative expression of CD48 protein or CD244 protein, in order to generate a purified cell sample, wherein the cells are selected from at least one of the following: $CD150^+$ cells, $CD48^-$ cells, and $CD244^-$ cells, and wherein the purified cell sample comprises a higher percent of HSCs than are present in the first sample. In particular embodiments, the present invention provides compositions purified by the above method.

In some embodiments, the present invention provides methods comprising; a) providing: i) a first cell sample comprising hematopoietic stem cells (HSCs), and ii) a device configured to collect desired cells from the first cell sample by identifying cells according to their positive or negative expression of cell surface proteins; and b) using the device to identify the desired cells from the first cell sample in order to generate a second cell sample, wherein the using the device involves assessing the presence or absence of at least one of the following proteins on the surface of cells within the first cell sample: CD150, CD48, or CD244, wherein the desired cells are HSCs, and wherein the desired cells are selected from at least one of the following: CD150+ cells, CD48– cells, or CD244– cells, and c) collecting in the second cell sample HSCs and other cells that are at least one of the following: CD150+, CD48−, or CD244−, wherein the second cell sample comprises a higher percent of HSCs than are present in the first cell sample.

In certain embodiments, the present invention provides compositions comprising an enriched cell sample, wherein the enriched cell sample comprises HSCs, and wherein at least 55% of the cells in the enriched cell sample are CD150+ HSCs. In further embodiments, at least 60%, or 70%, 80%, or 90% or 95% of the cells in the enriched cell sample are CD150+HSCs.

In other embodiments, the present invention provides an enriched cell sample, wherein the enriched cell sample comprises HSCs, and wherein at least 20% of the cells in the enriched cell sample are CD150+CD48− HSCs. In particular embodiments, at least 50%, 75%, or 90% of the cells in the enriched cell sample are CD150+CD48− HSCs.

In some embodiments, the present invention provides methods comprising: a) providing; i) a subject, and ii) a composition selected from the group consisting of: A) a first enriched cell sample comprising HSCs, wherein at least 60% of the cells in the first enriched sample are CD150+ HSCs; and B) a second enriched cell sample comprising cells, wherein at least 35% of the cells, when intravenously injected into the subject, are able to home to bone marrow and engraft; and b) treating the subject with the first enriched cell sample or the second enriched cell sample. In certain embodiments, the subject has been exposed to high dose chemotherapy. In particular embodiments, at least 80% of the cells in the first enriched cell sample are CD150+ HSCs. In some embodiments, at least 35% of the cells in the second purified cell sample are further able to provide long-term multi-lineage reconstitution.

In some embodiments, the desired cells are CD150$^+$ cells and the purified cell sample comprises a higher percentage of CD150$^+$ HSCs than are present in the test sample. In certain embodiments, the desired cells are CD48$^-$ cells and the purified cell sample comprises a higher percentage of CD48$^-$ HSCs than are present in the test sample. In particular embodiments, the desired cells are CD244$^-$ cells and the purified cell sample comprises a higher percentage of CD244$^-$ HSCs than are present in the test sample. In additional embodiments, the purified cell sample comprises greater than 1 percent CD150$^+$ HSCs. In further embodiments, the desired cells are CD150$^+$CD48$^-$ cells and the purified cell sample comprises a higher percentage of CD150$^+$CD48$^-$HSCs than are present in the test sample. In some embodiments, the purified cell sample comprises greater than 0.01 percent of CD150$^+$CD48$^-$ HSCs. In other embodiments, the desired cells are CD150$^+$CD48$^-$CD244$^-$ cells and the purified cell sample comprises a higher percentage of CD150$^+$CD48$^-$CD244$^-$ HSCs than are present in the test sample. In particular embodiments, the purified cell sample comprises greater than 0.01 percent of CD150$^+$CD48$^-$CD244$^-$HSCs. In some embodiments, the test sample is from a subject.

In particular embodiments, the present invention provides compositions comprising a purified cell sample, wherein the purified cell sample comprises HSCs, and wherein at least 55% of the HSCs in the purified cell sample are either CD150$^+$, CD48$^-$, or CD244$^-$. In other embodiments, at least 60% (or at least 65%, 70%, 75%, 80%, 85%, 90%, 95%, or 99%) of the HSCs in the purified cell sample are CD 150$^+$, CD48$^-$, or CD244$^-$.

In some embodiments, the present invention provides compositions comprising a purified cell sample, wherein the purified cell sample comprises cells, and wherein at least 30% of the cells, when intravenously or otherwise injected into an animal, are able to home to bone marrow and engraft. In other embodiments, the at least 30% of the cells are further able to provide long-term multi-lineage reconstitution. In further embodiments, at least 40% of the cells, when intravenously or otherwise injected, are able to home to bone marrow and engraft. In certain embodiments, the animal has been subject to myeloablative treatment. In particular embodiments, the at least 30% or 40% of the cells are CD150$^+$, CD48$^-$, or CD244$^-$, or any particular combination thereof.

In particular embodiments, the present invention provides methods comprising a) providing i) a subject, and ii) a composition selected from the group consisting of: A) a first purified cell sample comprising HSCs, wherein at least 50%, 55%, 60% and higher of the cells in the first purified sample are CD150+HSCs; and B) a second purified cell sample comprising cells, wherein at least 21%, 25%, 35%, 40% and higher of the cells, when intravenously injected into the subject, are able to home to bone marrow and engraft, b) treating the subject with the first or second purified cell sample. In some embodiments, the subject has been exposed to high dose or other chemotherapy. In certain embodiments, the subject is suffering from aplastic anemia.

In particular embodiments, the present invention provides methods comprising a) providing i) a test cell sample from a subject, wherein the test cell sample comprises hematopoietic stem cells (HSCs), ii) a purification device configured to purify HSCs or particular types of MPPs from the test cell sample based the presence or absence of no more than two, or no more than 3, or no more than 4 or 5 (or any combination) of the following SLAM family member proteins: CD150, CD84, CD229 (ly-9), CD244, NTB-A, CS1, CD48, CD58, CD2, 19A and Ly108.3; and b) using the purification device on the test cell sample under conditions such that a purified cell sample is generated, wherein the purified cell sample comprises a higher percent of HSCs or a particular type of MPPs than present in the test cell sample. In particular embodiments, the test sample is a hematopoietic tissue sample.

In some embodiments, the present invention provides methods comprising a) providing i) a test cell sample from a subject, wherein the test cell sample comprises hematopoietic stem cells (HSCs) and ii) a purification device configured to isolate, collect, or purify CD150+HSCs from the test cell sample; and b) contacting the test cell sample with the purification device under conditions such that a purified cell sample is generated, wherein the purified cell sample comprises a higher percent of CD150$^+$ HSCs than present in the test cell sample. In particular embodiments, the test sample is a hematopoietic tissue sample. In certain embodiments, the purification device is further configured to purify CD48$^-$ HSCs from the test sample, and wherein the purified cell sample further comprises a higher percent of CD48$^-$ HSCs than present in the test sample. In other embodiments, the test cell sample comprises whole bone marrow (WBM) cells, or cells from any other hematopoietic tissue sample.

In certain embodiments, the purified cell sample comprises at least 1.0% CD150$^+$ HSCs (e.g. of all the cells in the purified cell sample, at least 1.0% are CD150$^+$ HSCs). In some embodiments, the purified cell sample comprises at least 2.0% or at least 3.0% or at least 4.0% CD150$^+$ HSCs, or between 1% and 10% CD150$^+$ HSCs. In additional embodiments, the purified cell sample comprises greater than 5 percent CD150$^+$ HSCs (e.g. of all the cells in the purified cell sample at least 5.1 percent, about 6.0 percent, about 8.0 percent about 10 or greater, such as 5-15 percent are CD150$^+$ HSCs). In other embodiments, the purified cell sample comprises greater than 0.01 percent of CD150$^+$CD48$^-$ HSCs (e.g.

of all the cells in the purified cell sample at least 0.02 percent or 0.05 percent or 0.1 percent or 5 percent are CD150$^+$CD48$^-$ HSCs). In additional embodiments, the purified cell sample comprises greater than 0.01 percent of CD150$^+$CD48$^-$CD244$^-$ HSCs (e.g. of all the cells in the purified cell sample at least 0.02 percent or 0.05 percent or 0.1 percent or 5 percent are CD150$^+$CD48$^-$CD244$^-$ HSCs).

In certain embodiments, the purification device comprises a cytometer or similar device. In some embodiments, the purification device comprises anti-CD150 antibodies, antibody fragments, or other CD150 binding molecules. In other embodiments, the purification device comprises anti-CD48 antibodies, antibody fragments, or other CD48 binding molecules. In further embodiments, the purification device comprises anti-CD244 antibodies, antibody fragments, or other CD244 binding molecules. In certain embodiments, the subject is a human. In other embodiments, the subject is a mouse, rat, dog, cat, pig, cow or horse, other mammal, or bird.

In some embodiments, the present invention provides compositions comprising a purified cell sample, wherein the purified cell sample comprises greater than 1, 2, 3, 4, 5 or 10 percent CD150$^+$ hematopoietic stem cells (HSCs). In certain embodiments, the purified cell sample is a whole bone marrow cell sample or other hematopoietic tissue sample.

In other embodiments, the present invention provides compositions comprising a purified cell sample, wherein the purified cell sample comprises greater than 0.01 percent of CD150$^+$CD48$^-$ hematopoietic stem cells (HSCs). In particular embodiments, the purified cell sample is a whole bone marrow cell sample.

In certain embodiments, the present invention provides compositions comprising a purified cell sample, wherein the purified cell sample comprises a higher percentage of CD150$^+$ hematopoietic stem cells (HSCs) than present in an unpurified cell sample taken from a subject. In some embodiments, the purified cell sample comprises a higher percentage of CD48$^-$ HSCs than present in the unpurified cell sample taken from the subject. In certain embodiments, the purified cell sample comprises a higher percentage of CD244$^-$ HSCs than present in the unpurified cell sample taken from the subject. In particular embodiments, the unpurified cell sample comprises whole bone marrow cells.

In particular embodiments, the present invention provides methods comprising a) providing i) a subject, and ii) a composition selected from the group consisting of: A) a first purified sample comprising greater than 1, 2, 3, 4 or 5 percent CD150$^+$ hematopoietic stem cells (HSCs); B) a second purified sample comprising greater than 0.01 percent of CD150$^+$CD48$^-$ hematopoietic stem cells (HSCs); C) a third purified sample comprising a higher percentage of CD150$^+$ (or CD48$^-$ or CD244$^-$) hematopoietic stem cells (HSCs) than present in an unpurified cell sample taken from the subject; D) a fourth purified sample comprising greater than 0.01 percent of CD150$^+$CD48$^-$CD244$^-$ hematopoietic stem cells (HSCs); and b) treating the patient with the first, second, third, or fourth purified cell sample. In some embodiments, the subject has been exposed to high dose or other chemotherapy. In other embodiments, the subject is suffering from aplastic anemia. In further embodiments, the subject is a human, mouse, rat, cat, dog, pig, or horse, other mammal, or bird.

In other embodiments, the present invention provides devices configured for purifying CD150$^+$ HSCs from a test cell sample. In some embodiments, the present invention provides devices (e.g. cytometers) configured for purifying from a test sample HSCs that are CD150$^+$, CD48$^-$, or CD244$^-$ (or any combination thereof).

In some embodiments, the present invention provides kits comprising; a) reagents for targeting the expression or non-expression of CD150, CD48, or CD244 and b) an insert sheet comprising directions for employing the reagents to identifying or collecting HSCs that are CD150$^+$, CD48$^-$, or CD244$^-$ (or any combination thereof).

In other embodiments, the present invention provides methods comprising a) providing i) reagents for detecting HSCs that are CD150$^+$, CD48$^-$, or CD244$^-$ (or any combination thereof), and ii) a cell sample or a subject; and b) contacting the reagents with the cell sample or the subject such that the presence, absence or level of HSCs that are CD150$^+$, CD48$^-$, or CD244$^-$ (or any combination thereof) is determined.

In some embodiments, the present invention provides methods of generating an enriched cell sample comprising: purifying cells from a first sample based on the positive expression of CD 150 protein or negative expression of CD48 protein or CD244 protein, in order to generate an enriched cell sample that is enriched 2-fold (or 3-fold, 4-fold, 6-fold, 10-fold or 100-fold) in cells selected from the following: CD150$^+$ cells, CD48$^-$ cells, and CD244$^-$ cells, and wherein said enriched cell sample comprises a higher percent of HSCs than are present in said first sample.

In some embodiments, the present invention provides a purification device configured to collect HSCs from a test cell sample by identifying cells according to their positive expression of CD150 or negative expression of CD48 or CD244. In certain embodiments, the purification device comprising anti-CD150, anti-CD48, and/or anti-CD244 antibodies or antibody fragments (or other binding molecules).

DEFINITIONS

Figure 1:
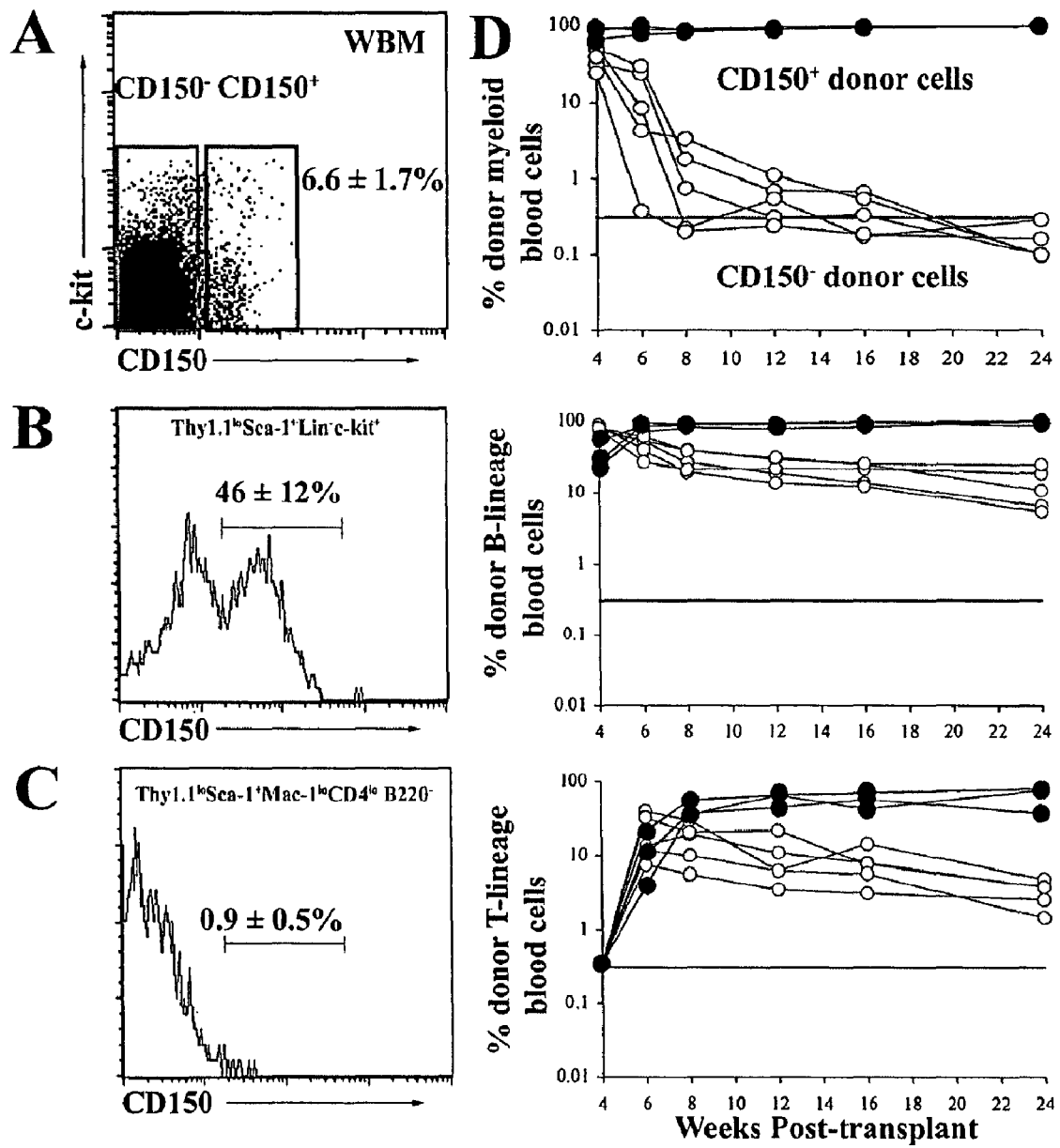
FIG. 1: The CD150$^+$ fraction of bone marrow cells is enriched for HSCs while the CD150$^-$ fraction contains transiently reconstituting multipotent progenitors. CD150 versus c-kit expression shows that only 6.6% of bone marrow cells express CD150 (A). CD150 expression was detected within the Thy-1$^{low}$Sca-1$^+$Lineage$^-$c-kit$^+$ HSC population (B) but not within the Thy-1$^{low}$Sca-1$^+$Mac-1$^{lo}$CD4$^{lo}$B220$^-$ MPP population (C). 20,000 CD150$^+$ bone marrow cells gave rise to long-term multilineage reconstitution in all recipients (D, filled circles), while 180,000 CD150$^-$ bone marrow cells gave transient multilineage reconstitution (D, open circles). Data are from one of two independent competitive reconstitution assays that gave similar results. Each line represents the frequency of donor-derived myeloid, B, or T cells in a single mouse. cDNA samples equivalent to 200 Thy-1$^{low}$Sca-1$^+$Lineage$^-$c-kit$^+$ HSCs, Thy-1$^{low}$Sca-1$^+$Mac-1$^{low}$CD4$^{low}$B220$^-$ MPPs, or whole bone marrow (WBM) cells were compared by quantitative (real-time) PCR. No differences were observed in hypoxanthine phosphoribosyltransferase (HPRT) expression between HSCs and MPPs, though HPRT levels were 3.2-fold lower in equivalent numbers of whole bone marrow cells (E). CD150 transcripts were present at 6.5-fold higher levels in HSCs as compared to MPPs and 39-fold higher levels in HSCs as compared to WBM cells (F). When these samples were normalized based on HPRT content, CD150 was present at 6.4-fold higher levels in HSCs as compared to MPPs and 12.5-fold higher levels as compared to WBM. Note that Table 2 presents qPCR results that are normalized based on HPRT content and which therefore underestimate differences between HSCs and WBM on a per cell basis. Each qPCR reaction generated a single amplicon with a homogeneous melting curve that formed a single band of the expected size on an agarose gel (G). Products on the gel were obtained after 35 cycles of PCR to illustrate the differences in CD150 amplification.
Figure 1:
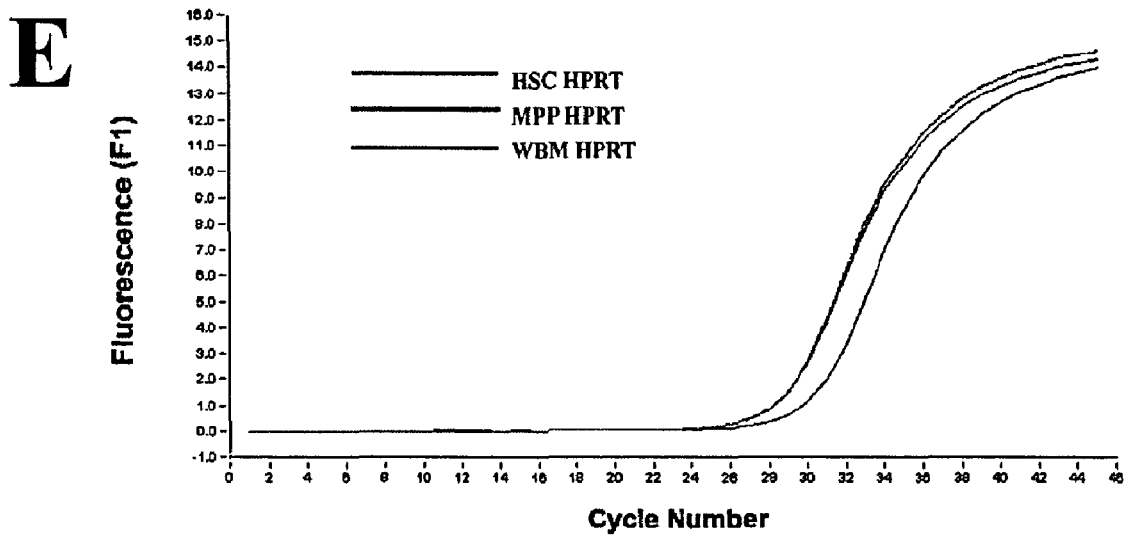
Figure 1:
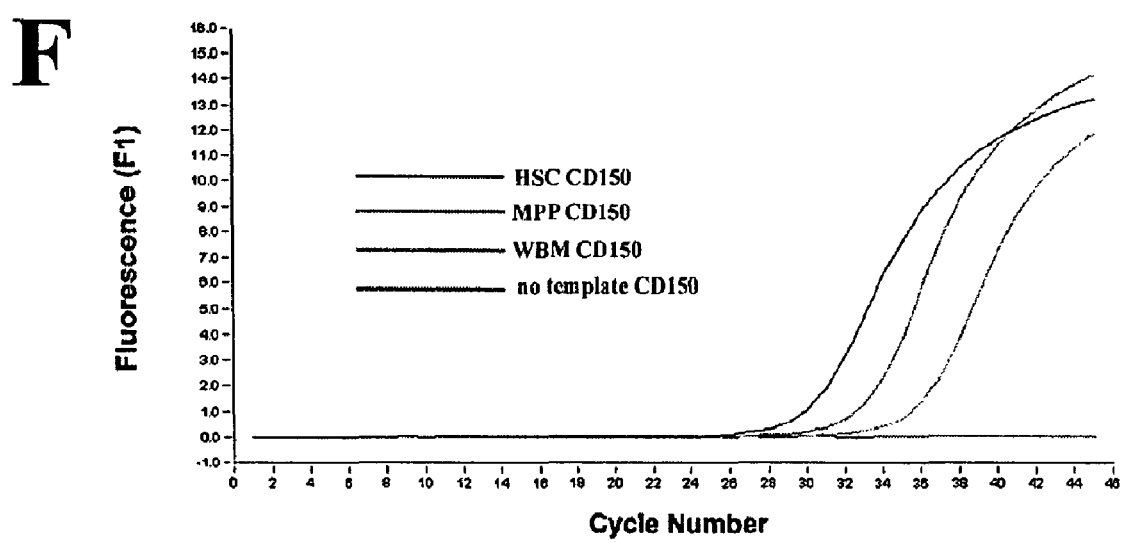
Figure 1:
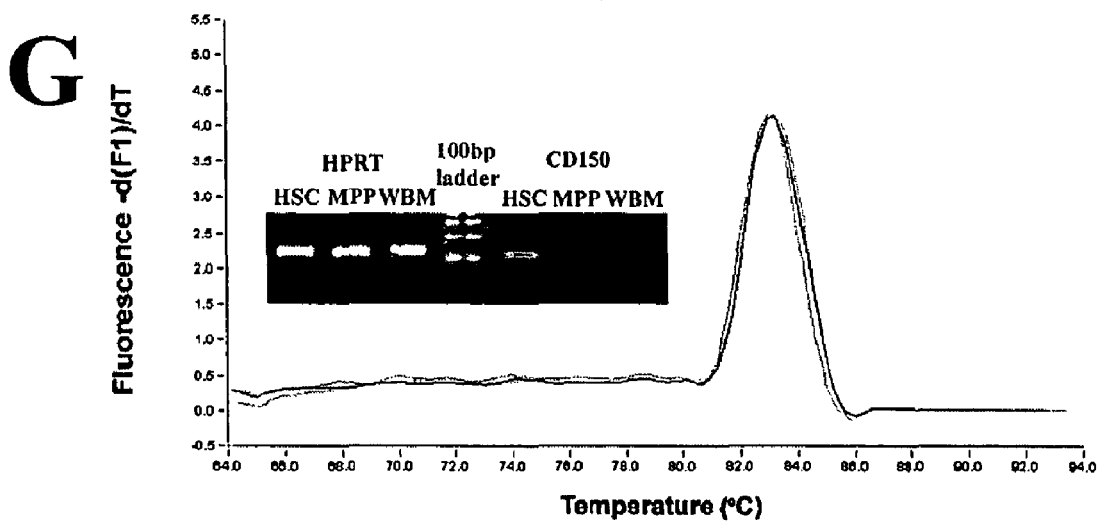

To facilitate an understanding of the invention, a number of terms are defined below.

As used herein, the terms "subject" and "patient" refer to any animal, such as a mammal like a dog, cat, bird, livestock, and preferably a human. Specific examples of "subjects" and "patients" include, but are not limited to, individuals who have been exposed to high dose chemotherapy.

As used herein, the term "treating" when referring to a subject, refers to administering the purified or enriched cell samples of the present invention to a subject, and may include, for example, bone marrow transplants (e.g., of cell samples originally from the subject or from a different subject) or any type of introduction of the cell samples of the present invention into or onto the body of a subject.

DETAILED DESCRIPTION

The present invention provides better and more efficient methods of identifying, isolating, or collecting hematopoietic stem cells (HSCs) and better and more easily created compositions containing high concentrations of HSCs. It has been determined that cells from bone marrow and other hematopoietic tissues that do not express the surface markers CD48 or CD244 but do express the surface marker CD150 makeup a highly purified population of HSCs and that using appropriate combinations of the expression patterns of these surface markers allows for the isolation and identification of a highly purified population of HSCs. Specifically, the present invention provides methods of isolating, identifying, or collecting CD150⁺ HSCs and CD150⁺CD48⁻ HSCs and CD48⁻ HSCs and CD150⁺CD244⁻ HSCs from within a sample of hematopoietic tissue. The present invention also provides purified hematopoietic tissue samples having an increased level of CD150⁺ HSCs and CD150⁺CD48⁻ HSCs and CD48⁻ HSCs and CD150⁺CD244⁻ HSCs. The present invention further provides methods of treating or evaluating the treatment of subjects by making use of such methods and compositions. The methods of the present invention, for example, can make use of known separation techniques and bioassays for identification, quantification or physical separation of HSCs from non-HSC cells within a hematopoietic tissue sample. The methods and compositions of the present invention may be employed advantageously in a wide variety of clinical and research applications and settings. For convenience, the detailed description is provided in the following sections below: (I) Hematopietic Stem Cells; (II) Exemplary Sources of Hematopoietic Tissue Samples Containing HSCs; (III) Exemplary HSC Purification Techniques; and (IV) Exemplary Embodiments.

I. Hematopoietic Stem Cells

Hematopoietic stem cells (HSCs) are responsible for the production of mature blood cells throughout fetal and adult life. HSCs are characterized by their ability to self-renew and undergo long-term multilineage differentiation to form all lineages of blood cells including but not limited to B-cells, T-cells, myeloid cells (macrophages and granulocytes), platelets and red blood cells. In fetal development HSCs exist in the peripheral blood, the umbilical cord blood vessels, the placenta, the aorto-gonado-mesonephros, the fetal liver and spleen, and, eventually, the developing bone marrow cavities. In the adult, HSCs reside largely in the bone marrow cavities under physiological conditions. HSCs in adults have also been shown to circulate in very low frequencies through the vasculature existing in both the spleen and skeletal muscle. The circulation of HSCs through the circulatory system may be induced using a mobilization procedure such as cyclophosphamide followed by G-CSF treatment (CY/G-CSF), which expands the number of HSCs in the blood and in spleen tissue.

Whereas HSCs are capable of self-renewal and long-term multilineage differentiation, other hematopoietic progenitor cells capable of giving rise to cells of mature blood lineages after transplantation or in cultures are not capable of self-renewal and produce mature blood cells only transiently. These other hematopoietic progenitor cells, which encompass MPPs, are therefore incapable of sustaining long-term hematopoiesis. For example, HSCs give rise to other HSCs following cell division under certain conditions also give rise to non-self-renewing multipotent progenitors (MPPs) that can be isolated from murine hematopoietic tissue as Thy-$1.1^{lo}$Sca-$1^+$Mac-1loCD4lo (See, Morrison et al., 1994 and Morrison et al. 1997 supra). These cells give rise to myeloid, B and T cells for less than 12 weeks after injection into irradiated recipients. However, MPPs are not able to give rise to a sufficient number of other MPPs to sustain long-term hematopoiesis and are therefore considered to not be able to undergo self-renewal.

Tissue and cell samples containing HSCs can be transplanted into diseased, chemotherapeutically conditioned, or lethally (or sublethally) irradiated recipients rescuing the recipients from death owing to hematopoietic failure or compromise, which can result in overwhelming infection or inadequate erythropoiesis. Generally, to be effective clinically, such samples must first be purified to isolate, and obtain artificially high concentrations of, HSCs, for example, by detecting expression of specific cell surface proteins or receptors, cell surface protein markers, or other markers. Highly purified HSCs are increasingly being used clinically, in a variety of applications, such as for autologous transplants into patients after high-dose chemotherapy. In this setting it is advantageous to isolate HSCs with the maximum degree of purity so as to minimize contamination by immune effector cells (such as lymphocytes) or cancer cells. Since few markers have been identified that are highly specific to HSCs, however, it has previously not been possible to achieve the required degree of purity based on simple combinations of one or two markers associated with cell surface proteins. As a result, it has been possible to highly purify or identify HSCs only by making use of complex combinations of many markers. In murine studies, the highest enrichment of HSC activity yet reported describes combinations of markers, such as those used to isolate Thy-$1.1^{lo}$Sca-$1^+$lineage$^-$Mac-$1^-$CD4$^-$c-kit$^+$ cells (hereafter referred to as Mac-$1^-$CD4$^-$c-kit$^+$), from which about one out of every five intravenously injected cells are able to home to bone marrow and engraft. Such results are described in, for example, Uchida et al.; Morrison et al., 1994 and Morrison et al. 1997 supra). Likewise, current techniques employed to isolate the purest population of stem cells in human hematopoietic samples require the use of as many as 12 different clones of antibodies.

These complex combinations of markers have not been practical to use clinically, however, owing to considerations including high cost and excessive tissue handling. As a result, simplified combinations of one or two markers (e.g. markers used to target CD34$^+$ or CD34$^+$CD38$^-$ cells) have often been used for the clinical isolation or identification of HSCs, but these simplified combinations yield much lower levels of purity and may not purify or identify all HSCs within a population of hematopoietic tissue (HSCs can be shown to have heterogenous expression pattern of CD34 see e.g. U.S. Pat. No. 6,353,150, herein incorporated for all purposes).

As a result of the recognized short comings of existing marker combinations, including inadequate recovery of all HSC activity from within a hematopoietic tissue sample, additional expense associated with the use of many different clones of antibodies or the inability to adequately purify HSCs from non-HSC cells within a starting cell sample, it would be desirable to identify new cell surface proteins and markers that improve and simplify the purification and identification of HSCs to facilitate their study and clinical use. The present invention provides such methods and compositions.

II. Exemplary Sources of Hematopoietic Tissue Samples Containing HSCs

The hematopoietic tissue samples for use in various embodiments of the present invention are not limited by source or origin. Such samples can be taken from a subject to be treated or from another individual. Hematopoietic tissue for the identification or isolation of HSCs may include but is not limited to bone marrow, isolated from sternum, iliac crests, femora or other bone marrow cavities. Other sources include any tissue which contains any amount of HSCs but may have only endogenously low frequencies of HSCs. These tissues may include but are not limited to embryonic yolk sac, fetal liver or spleen, adult spleen or treated or untreated peripheral blood, and umbilical cord blood. Cells may be collected by physically or enzymatically or chemically dissociating cells in single cell suspension such that a majority of cells to be further processed are no longer attached to other cells from within the original hematopoietic tissue sample whether through direct cell-cell interactions or indirectly through extracellular connective tissue. Cells may be processed further in an appropriate isoosmotic salt solution such as phosphate buffered saline (PBS) or Hank's buffered saline solution (HBSS; as described herein) which may or may not contain protein in the form of BSA or serum and which may or may not contain chemicals buffers to maintain physiological pH.

HSCs may be acquired from primary hematopoietic tissue or alternatively may be isolated or identified prior to culture under conditions conducive to the expansion of hematopoietic progenitors such as by culturing in hematopoietic bioreactors or by supplementation with SCF or by co-culturing with stromal elements supportive of hematopoietic progenitor cell expansion or survival or by culturing in media conditioned by being previously inoculated onto stromal feeder layers which secrete factors and proteins conducive to the maintenance and survival and expansion of HSCs. For example, hematopoietic tissue samples appropriate for use according to the present invention include tissue samples that have been pre-sorted for HSCs (or MPPs) according to known or other sorting techniques such as sorting for CD34 expression or pre-enriching by density elutriation among other things.

III. Exemplary HSC Purification Techniques

The present invention is not limited by the purification technique or device that takes advantage of the presence or absence of SLAM family member proteins (e.g. CD150, CD48, CD244, or any combination thereof) on HSCs, MPPs, or other hematopoietic cells. Any method suitable for identifying surface proteins, whether known or to be discovered, could be employed in the various methods of the present invention. For example, HSCs according to the present invention may be identified using fluorescence activated cell sorting analysis (FACS) which typically uses antibodies conjugated to fluorochromes to directly or indirectly assess the level of expression of a given surface protein on individual cells within a heterogenous (or homogenous) cell preparation of hematopoietic tissue. The expression of or lack of expression of the SLAM family member surface proteins, in particular, CD150, CD48 and CD244 on individual cells within the cell preparation may also be assessed using means other than antibody-antigen interaction or fluorescence detection or FACS. HSCs may be physically separated from other cells within a cellular preparation of hematopoietic tissue using any previously developed or as yet undeveloped technique whereby cells are directly or indirectly differentiated according to their expression or lack of expression of SLAM-family member surface proteins CD150, CD48, CD244, as well as CD84, CD229, NTB-A, CS1, CD58, CD2, 19A or Ly108.3. Positive selection or negative selection may be employed to enrich for or deplete of, respectively, cells which do or do not express the SLAM-family member cells surface markers (e.g. CD150, CD48, or CD244). Common methods used to physically separate specific cells from within a heterogenous population of cells within a hematopoietic cell preparation include but are not limited to flow-cytometry using cytometer which may have varying degrees of complexity and or detection specifications, magnetic separation, using antibody or protein coated beads, affinity chromatography, or solid-support affinity separation where cells are retained on a substrate according to their expression or lack of expression of a specific protein or type of protein. Such separation techniques need not, but may, completely purify or nearly completely purify (e.g. 99.9% are perfectly separated) HSCs or populations enriched in HSCs according to expression or lack of expression of SLAM family members.

IV. Exemplary Embodiments

Various embodiments of the present invention involve the steps of obtaining a hematopoietic tissue sample containing HSCs and/or MPPs, identifying desired cells such as HSCs or particular MPPs from within the sample based on their expression or lack of expression of particular SLAM family member proteins. For example, in preferred embodiments, the methods involve identifying those cells from within a sample that express CD150, do not express CD48, and do not express CD244 (or any combination of these expression characteristics), isolating or collecting the identified cells for quantification, further examination and study, or for use in treatment of a wide variety of medical conditions.

The methods and compositions of the present invention can be employed advantageous in a wide variety of applications. In any application where HSCs, or the identification thereof, are useful, the methods and compositions of the present invention can be used. For example, purified HSCs as described in this invention would be useful in bone marrow transplantation as well as mobilized peripheral blood or umbilical cord blood transplantation as well as the transplantation of other organs in association with the transplantation of bone marrow; for the prospective identification and quantification of HSCs resident in unfractionated bone marrow or other hematopoietic tissue transplants or to monitor the progress of a patient's hematopoietic tissue transplantation or chemotherapeutic treatment; for the purposes of studying the properties of HSCs including their response to various growth factors, their production of growth factors, their interaction with stromal elements, etc; for the introduction, amplification and/or modification of endogenous or exogenous genes or gene elements to promote the health of recipients of transplanted HSCs; for the treatment of leukemias or lymphomas, as well as other neoplastic conditions, e.g. breast cancer. HSCs according to the methods and compositions of the present invention would also find use 1) in regenerating the hematopoietic system of a host deficient in HSCs, 2) in a host that is diseased and can be treated by removal of bone marrow or other hematopoietic tissue containing HSCs, isolation of HSCs and treatment of individuals with pharmaceuticals or irradiation prior to re-infusion of HSCs, 3) producing various hematopoietic cells in vivo or in vitro, 4) the development of hematopoietic cell lineages and assaying for factors or biological properties including gene expression profiles associated with hematopoietic development, and 5) treatment of genetic diseases through replacement, amplification, modification or inhibition of genes or gene elements, for example.

In certain embodiments, the identification of HSCs, with or without later transplantation or reconstitution using the identified HSCs, can be useful in itself. Identification of HSCs within a hematopoietic tissue sample or cell preparation derived from a hematopoietic tissue sample may be useful for assessing the ability of a sample of hematopoietic cells to give rise to engraftment and reconstitution in patients undergoing bone marrow transplantation; for monitoring the progress of recovery from myeloablative treatment or other therapy damaging to hematopoietic tissues such as irradiation or chemothereutic protocols; for assessing the HSC content of hematopoietic cultures; for monitoring the progress, assessing the status of or ascertaining the prognosis for the disease of a patient having a disorder of the hematopoietic system such as aplastic anemia or lymphoma or a neoplastic disorder such as leukemia or diseases conferring immunocompromise; and for treatment of intractable disorders associated with autoimmunity such as systemic lupus erythematosus, for example.

The methods and compositions of the present invention can also be employed advantageously in combination with gene therapy and other genetic techniques. HSCs may be used for the treatment of genetic diseases or for the treatment of diseases which may be ameliorated by modification of gene expression within a host. Genes or gene elements may be introduced, inhibited, removed, modified, or otherwise altered in the HSCs of patients undergoing autologous or allogeneic HSC or hematopoietic cell transplant. Genetic manipulation of HSCs may be useful for treatment of genetic diseases associated with the hematopoietic system such as the red blood cell dyscrasias, beta-thalassemia, sickle cell anemia, adenosine deaminase deficiency or diseases associated with clotting factor deficiency such as hemophilia or diseases associated with immunocompromise such as recombinase deficiency or severe-combined immuno-deficiency syndrome. Genetic manipulation of HSCs may also be useful for treatment of non-hematopoietic disorders where the disease is associated with the absence of an appropriately expressed or appropriately secreted protein product such as a hormone or enzyme. Alternatively, genes or gene elements may be introduced into HSCs which will then produce or modify chemicals or biological molecules not limited to secreted proteins. HSCs from individuals not diagnosed with disease may be used for the treatment of a patient's disorder in allogeneic transplant or a patient's own HSCs may be genetically modified to correct or ameliorate the effects of the disorder. Introduction of foreign genes or gene elements may be achieved by using live, attenuated or killed measles virus particles, portions of live, attenuated or killed measles virus particles or other viral vector typically used for the introduction of genes or gene elements into mammalian cells. Genes or gene elements may also be introduced into HSCs by using the ability of self-ligating properties of CD150 (or other proteins) across the membranes of two separate cells expressing CD150 or the self-liganding properties of CD150 within the membrane of an individual cell expressing CD150 protein.

Treatment of hematopoietic tissue including HSCs with certain clones of anti-CD150 antibodies may be used to activate or modify gene expression or augment or alter the biological activity of HSCs or may disrupt the interaction of CD150 on the surface of HSCs and on the surface of other cellular elements within hematopoietic tissue or hematopoietic stromal co-culture to modulate the ability of said co-culture to maintain or expand numbers of HSCs within said co-culture. Treatment of hematopoietic tissue or HSCs with certain clones of anti-CD150 antibodies may also be used disrupt or augment the ability of HSCs to home to and engraft in hematopoietic microenvironments suitable for the maintenance and expansion of HSCs.

In addition to identifying HSCs from within hematopoietic tissue samples, the techniques of the present invention, can be employed for the identification, isolation, or collection of MPPs. Accordingly, in addition to being able to isolate HSCs capable of long-term multilineage engraftment in vivo or hematopoietic cell production in vitro using expression patterns of SLAM family members, MPPs capable of only transient reconstitution in vivo and only transient hematopoietic cell production in vitro may be purified according to their expression of SLAM-family members. For example, MPPs may be identified or isolated as cells which do not express CD150, or which do not express CD48 or which do or do not express CD244. Isolation or identification of MPPs from within a heterogenous cell preparation from a hematopoietic sample may be useful when only transient production of blood cells is desired or when more rapid reconstitution is beneficial to the recipients; for assessing the ability of a sample of hematopoietic cells to give rise to engraftment and reconstitution in patients undergoing bone marrow transplantation; for monitoring the progress of recovery from myeloablative treatment or other therapy damaging to hematopoietic tissues such as irradiation or chemotherapeutic protocols; and for assessing the MPP content of hematopoietic cultures as described previously for HSCs; for monitoring the progress, assessing the status of or ascertaining the prognosis for the disease of a patient having a disorder of the hematopoietic system, among other things; for the transplant of MPPs into subjects alone or in combination with prior or subsequent transplantation of HSCs.

The present invention may also be employed to isolate and identify mesenchymal and nervous system progenitors. Progenitors from tissues other than hematopoietic tissue may be isolable or identifiable by their expression pattern of SLAM family members including but not limited to CD150, CD48 and or CD244. The sub-ventricular zone (sVZ) and the developing fetal forebrain (FB) have been shown to contain cells capable of generating large numbers of neurons and glial-lineage cells within the central nervous system. A certain proportion of cells resident within the sVZ of adult animals and within the FB of fetal animals express the SLAM family members CD150; certain of these cells expressing CD150 also express CD48 whereas certain others of these cells do not express CD48. Additionally, stromal cells resident within the bone marrow including but not limited to cells of the osteoblastic lineage which are the precursors to mature bone cell osteocytes and have been shown to support the maintenance and expansion of HSC numbers may be isolable or identifiable according to their expression of CD150. Osteoblastic cells within adult bone marrow have been shown to express N-cadherin but not the hematopoietic surface marker CD45. A population of cells exists which expresses N-cadherin, which does not express CD45 and which does express CD150 exists within the adult bone marrow cavity and may be demonstrated to be useful for production of stromal cells supportive of HSCs maintenance or expansion in vitro or for the production of osteocytes or graftable bone tissue precursors.

EXPERIMENTAL

The following experimental examples are provided in order to demonstrate and further illustrate various aspects of certain embodiments of the present invention and are not to be construed as limiting the scope thereof. In the experimental disclosure which follows, the following abbreviations apply: μg (micrograms); ng (nanograms); ml (milliliters); C (degrees Centigrade).

Example 1

The following example describes a study involving the microarray comparison of highly enriched populations of hematopoietic stem cells (HSCs) and multipotent progenitors (MPPs), and our determination that CD150 is expressed by HSCs. This example also describes HSC identification and purification employing antibodies which recognize CD150 and CD48 and CD244 on the surface of hematopoietic cells.

In an effort to identify genes that are closely associated with HSC identity, the gene expression profiles of highly enriched populations of HSCs and non-self-renewing multipotent progenitors (MPPs) were compared. Because the quality of gene expression profiles depends critically on the purity of the stem cells used in the analysis we characterized the purity of Thy-$1^{low}$Sca-$1^+$Lineage$^-$c-kit$^+$ HSCs prior to performing gene expression profiling on these cells. To evaluate the clonogenicity of single cells in culture, individual Thy-$1^{low}$Sca-$1^+$Lineage$^-$c-kit$^+$ cells were sorted into methylcellulose supplemented with Steel factor, IL-3, IL-6, erythropoietin, Flt-3, and thrombopoietin. 93±3% of single cells formed colonies in methylcellulose, 23±9% of which were CFU-GEMM, 64±11% of which were CFU-GM, and 13±5% were CFU-Meg. To assess their developmental potential in vivo a limit-dilution and competitive reconstitution experiments were performed to evaluate their ability to reconstitute irradiated recipients. 1 out of every 4.1±1.4 i.v. injected Thy-$1^{low}$Sca-$1^+$Lineage$^-$c-kit$^+$ cells detectably reconstituted, and 93±6% of recipients were long-term multilineage reconstituted (Table 1). This indicates that Thy-$1^{low}$Sca-$1^+$Lineage$^-$c-kit$^+$ cells are highly enriched for long-term self-renewing HSCs.

TABLE 1

Thy-1$^{low}$Sca-1$^+$Lineage$^-$c-kit$^+$ cells are highly enriched for long-term reconstituting, multipotent HSCs.

| Cells injected | Mice that engrafted | Frequency of cells that engrafted | Engrafted mice with long-term multilineage reconstitution | Frequency of cells that long-term multilineage reconstituted (HSCs) |
|---|---|---|---|---|
| 10 | 24/28 | 1 in 5.7 | 88% (21/24) | 1 in 7.7 (21/28) |
| 5 | 13/15 | 1 in 3.0 | 100% (13/13) | 1 in 3.0 (13/15) |
| 4 | 25/34 | 1 in 3.5 | 92% (23/25) | 1 in 4.1 (23/34) |
| Mean ± SD | 82 ± 7% | 1 in 4.1 ± 1.4 | 93 ± 6% | 1 in 4.9 ± 2.5 |

In regard to Table 1, the indicated number of donor-type (CD45.1$^+$) Thy-1$^{low}$Sca-1$^+$Lineage$^-$c-kit$^+$ cells were transplanted intravenously into lethally irradiated recipients (CD45.2$^+$) along with 200,000 recipient-type (CD45.2$^+$) whole bone marrow cells for radioprotection. Recipients were considered engrafted by donor cells if any CD45.1$^+$ cells were detected in their peripheral blood (above background: >0.1-0.3% of myeloid cells or >0.1-0.15% of lymphoid cells, depending on the experiment) at least 4 weeks after reconstitution. The frequency of cells that engrafted was calculated based on limit-dilution (Poisson) statistics. Mice were considered long-term multilineage reconstituted if donor-type myeloid, B, and T cells were present for more than 16 weeks after reconstitution.

Thy-1$^{low}$Sca-1$^+$Lineage$^-$c-kit$^+$ HSCs give rise to non-self-renewing MPPs in vivo (Morrison et al. 1997, supra), prior to undergoing lineage restriction. These MPPs are highly enriched in the Thy-1$^{low}$Sca-1$^+$Mac-1$^{low}$CD4$^{low}$ population. In previous studies, only 26% of Thy-1$^{low}$Sca-1$^+$Mac-1$^{low}$CD4$^{low}$ cells formed myeloerythroid colonies in methylcellulose cultures, and many clones gave rise to only B lineage reconstitution in vivo (Morrison et al. 1994 and Morrison et al. 1997). We found that 55±14% expressed the B cell marker B220 and furthermore that the B220$^+$ subset of Thy-1$^{low}$Sca-1$^+$Mac-1$^{low}$CD4$^{low}$ cells lacked the ability to form colonies in methylcellulose or to give multilineage reconstitution in vivo (data not shown), while the B220$^-$ subset was highly enriched for transiently reconstituting multipotent progenitors. 89±2% of single Thy-1$^{low}$Sca-1$^+$Mac-1$^{low}$CD4$^{low}$B220$^-$ formed myeloerythroid colonies in methylcellulose cultures and 98±0.7% of these colonies were CFU-GM. In competitive reconstitution assays in which 4 Thy-1$^{low}$Sca-1$^+$Mac-1$^{low}$CD4$^{low}$B220$^-$ cells were injected into each of 16 irradiated recipients, 1 out of every 4.0 i.v. injected cells detectably reconstituted. Of the 11 recipients that were reconstituted with donor cells, 64% were transiently multilineage reconstituted (M+B+T for <8 weeks), 27% were reconstituted only in the B and T lineages, and 9% were reconstituted only in the B lineage. These results are consistent with previously published results indicating that Thy-1$^{low}$Sca-1$^+$Mac-1$^{low}$CD4$^{low}$ cells reconstitute transiently and lack detectable self-renewal potential (Morrison et al., 1997). This indicates that Thy-1$^{low}$Sca-1$^+$Mac-1$^{low}$CD4$^{low}$B220$^-$ cells are more highly enriched for MPPs than any previously characterized cell population.

It was concluded that the best way of identifying genes that were highly restricted in their expression to HSCs, was to find genes that were expressed at significantly higher levels in HSCs as compared to both MPPs and CD45$^+$ bone marrow cells (which include nearly all hematopoietic cells). Three 3 independent 5,000 cell aliquots of HSCs or MPPs or 8,000 CD45$^+$ bone marrow cells (because these cells have a lower RNA content) were isolated, and independently extracted and amplified RNA from each aliquot for gene expression profiling (Iwashita et al., Science 2003; 301:972). The gene expression profiles were compared using AFFYMETRIX mouse genome oligonucleotide arrays. The variability was low among samples of the same type: Pearson correlation coefficient, $R^2$=0.988 to 0.991 for untransformed data. However, the variability between samples of different types (HSC versus MPP, $R^2$=0.798±0.024; HSC versus CD45$^+$, $R^2$=0.558±0.009) was significantly higher (P<0.0005). Transcript expression was detected (present calls) at 46% of probe sets for HSC, 46% of probe sets for MPPs, and 41% of probe sets for CD45$^+$ cells, then identified genes for which signal intensities were at least 3-fold higher in HSCs, the difference was statistically significant (P<0.05), and signals were significantly above background in at least one HSC sample (non-zero present call). 1151 probe sets were identified that satisfied these criteria for being upregulated in HSCs as compared to CD45$^+$ cells, and 46 probe sets against unique genes in HSCs as compared to MPPs (out of 36,701 probe sets total). Twenty-seven of these 46 probe sets were expressed at higher levels in HSCs as compared to both MPPs and CD45$^+$ cells. To further evaluate these candidates, their expression was compared by quantitative (real-time) RT-PCR in at least two independent samples of HSCs, MPPs, and whole bone marrow cells. Of the 25 genes against which qPCR primers could be designed, all were confirmed as being expressed at >1.9-fold higher levels in HSCs as compared to MPPs and CD45$^+$ cells (Table 2).

TABLE 2

Genes that were expressed at higher levels in HSCs as compared to MPPs and CD45$^+$ cells by both microarray analysis and quantitative PCR.

| | | | Microarray | | qPCR | |
|---|---|---|---|---|---|---|
| Probe set | Unigene Title | Unigene ID | HSC/MPP | HSC/CD45$^+$ | HSC/MPP | HSC/WBM |
| Clca1 | chloride channel calcium activated 1 | Mm.275745 | 8.3 | 9.1 | 32.8 | 3.3 |
| Cpne8 | Copine VIII | Mm.290991 | 7.0 | 11.0 | 3.8 | 29.9 |
| Sdpr | serum deprivation response | Mm.255909 | 7.0 | 7.0 | 116.7 | 40.3 |
| Catnal1 | catenin alpha-like 1 | Mm.218891 | 6.9 | 8.8 | 4.0 | 26.2 |
| Prkcm | protein kinase C, mu | Mm.282880 | 6.4 | 7.0 | ND | ND |
| Vwf | Von Willebrand factor homolog | Mm.22339 | 6.2 | 17.2 | 5.2 | 4.2 |
| Est | RIKEN full-length library, clone: E330020H17 | Mm.156641 | 5.7 | 5.7 | 4.9 | 2.8 |
| Mjd | Machado-Joseph disease homolog | Mm.271914 | 5.2 | 5.9 | 1.9 | 2.3 |
| Ly64 | lymphocyte antigen 64 | Mm.3177 | 4.8 | 13.7 | 9.0 | 53.8 |
| D10Ertd755e | DNA segment, Chr 10, ERATO Doi 755, expressed | Mm.208120 | 4.7 | 4.7 | ND | ND |

TABLE 2-continued

Genes that were expressed at higher levels in HSCs as compared to MPPs and CD45+ cells by both microarray analysis and quantitative PCR.

| | | | Microarray | | qPCR | |
|---|---|---|---|---|---|---|
| Probe set | Unigene Title | Unigene ID | HSC/MPP | HSC/CD45+ | HSC/MPP | HSC/WBM |
| C530008M17Rik | RIKEN cDNA C530008M17 gene | Mm.101504 | 4.7 | 7.4 | 15.3 | 2.9 |
| Est | *Mus musculus* transcribed sequences | Mm.37461 | 4.1 | 10.7 | 1.9 | 2.8 |
| Slam | signaling lymphocyte activation molecule | Mm.103648 | 4.0 | 4.0 | 5.8 | 17.0 |
| Est | *Mus musculus* transcribed sequences | Mm.22941 | 3.6 | 9.7 | 5.6 | 7.0 |
| 4930553F04Rik | RIKEN cDNA 4930553F04 gene | Mm.45980 | 3.6 | 6.0 | 2.4 | 2.9 |
| Peg12 | paternally expressed 12 | Mm.90135 | 3.6 | 3.8 | 9.2 | 22.9 |
| Bgn | biglycan | Mm.2608 | 3.5 | 64.1 | 7.7 | 52.6 |
| 2610104C07Rik | RIKEN cDNA 2610104C07 gene | Mm.289086 | 3.4 | 7.8 | 2.5 | 2.6 |
| Stub1 | STIP1 homology and U-Box containing protein 1 | Mm.277599 | 3.4 | 5.0 | 2.5 | 2.2 |
| Gemin4 | gem (nuclear organelle) associated protein 4 | Mm.127482 | 3.4 | 5.4 | 2.8 | 5.9 |
| Tfpi | tissue factor pathway inhibitor | Mm.124316 | 3.2 | 4.9 | 4.6 | 9.2 |
| Est | Weak similarity to NP_032607.1 melanoma Ag | Mm.206337 | 3.2 | 16.9 | 3.4 | 10.2 |
| pbx1 | Pre B-cell leukemia transcription factor 1 | Mm.43358 | 3.1 | 4.3 | 3.5 | 15.6 |
| 4432411H13Rik | RIKEN cDNA 4432411H13 gene | Mm.5162 | 3.1 | 14.7 | 7.0 | 6.1 |
| Ppap2b | phosphatidic acid phosphatase type 2B | Mm.27363 | 3.1 | 3.7 | 2.5 | 2.9 |
| 3010033I09Rik | RIKEN cDNA 3010033I09 gene | Mm.289674 | 3.0 | 3.1 | 5.6 | 34.0 |
| LOC215789 | hypothetical protein LOC215789 | Mm.100282 | 3.0 | 4.0 | 1.9 | 3.0 |

In regard to Table 2, cRNA from Thy-1$^{low}$Sca-1$^+$Lineage$^-$c-kit$^+$HSCs, Thy-1$^{low}$Sca-1$^+$Mac-1$^{low}$CD4$^{low}$B220$^-$ MPPs, or CD45$^+$ bone marrow cells were hybridized to oligonucleotide arrays. The average untransformed probe intensities from three independent samples were used to calculate fold-change (HSC/MPP; HSC/CD45$^+$). The table lists all of the genes that were expressed at significantly higher levels in HSCs as compared to MPPs and CD45$^+$ cells by both microarray analysis (fold change>3) and quantitative (real-time) PCR (fold change>1.9).

One of the few genes that was strongly upregulated in HSCs as compared to MPPs and CD45$^+$ cells, CD150, was particularly intriguing because it was not identified as being expressed or upregulated in stem cells in any previously published studies of which the inventors are aware. CD150 appeared to be 4-fold upregulated in HSCs as compared to MPPs and CD45$^+$ bone marrow cells by microarray analysis (Table 2), though this is likely an underestimate of the difference in expression since CD150 was not detectable in MPPs or CD45$^+$ cells by microarray (therefore these samples were set to 100 for the purpose of calculating fold-change (Iwashita et al., 2003). By qPCR, CD150 was upregulated in HSCs by 5.8±1.8-fold as compared to MPPs and 17.0±4.0-fold as compared to whole bone marrow cells (Table 2; FIG. 1).

To test whether CD150 was differentially expressed among HSCs and MPPs at the protein level, whole bone marrow cells were stained with an antibody against CD150. Only 6.6±1.7% of whole bone marrow cells were CD150$^+$ (FIG. 1A). Consistent with the trends observed at the RNA level (Table 2), CD150 was expressed by 46±12% of cells within the Thy-1$^{low}$Sca-1$^+$Lineage$^-$c-kit$^+$ HSC population but by only 0.9±0.5% of cells in the Thy-1$^{low}$Sca-1$^+$Mac-1$^{low}$CD4$^{low}$B220$^-$ MPP population (FIG. 1B,C).

To functionally test whether CD150$^+$ cells included HSCs, we performed competitive reconstitution assays in which 20,000 donor-type CD150$^+$ cells or 180,000 donor-type CD150$^-$ bone marrow cells (cell doses were based on the fraction of 200,000 whole bone marrow cells that were CD150$^+$ or CD150$^-$ as in prior HSC marker studies (Uchida et al., supra) transplanted into lethally irradiated recipients along with a radioprotective dose of 200,000 recipient-type whole bone marrow cells (FIG. 1D). In each of two independent experiments, recipients of the CD150$^+$ cells were always long-term multilineage reconstituted by donor cells (6/6 recipients) while recipients of the CD150$^-$ cells usually (8/9 recipients) exhibited transient multilineage reconstitution. Since 30,000 C57BL whole bone marrow cells yield long-term multilineage reconstitution in around 60% of recipients (Uchida et al., J Exp Med. 1992 Jan. 1; 175(1):175-84), these data indicate that HSCs are enriched in the CD150$^+$ fraction and depleted in the CD 150$^-$ fraction of bone marrow cells. Recipients of CD150$^+$ whole bone marrow cells were consistently able to transfer long-term multilineage donor cell reconstitution to secondary recipients, while recipients of CD150$^-$ cells were not able to transfer donor cell reconstitution to secondary recipients (data not shown).

Figure 2:
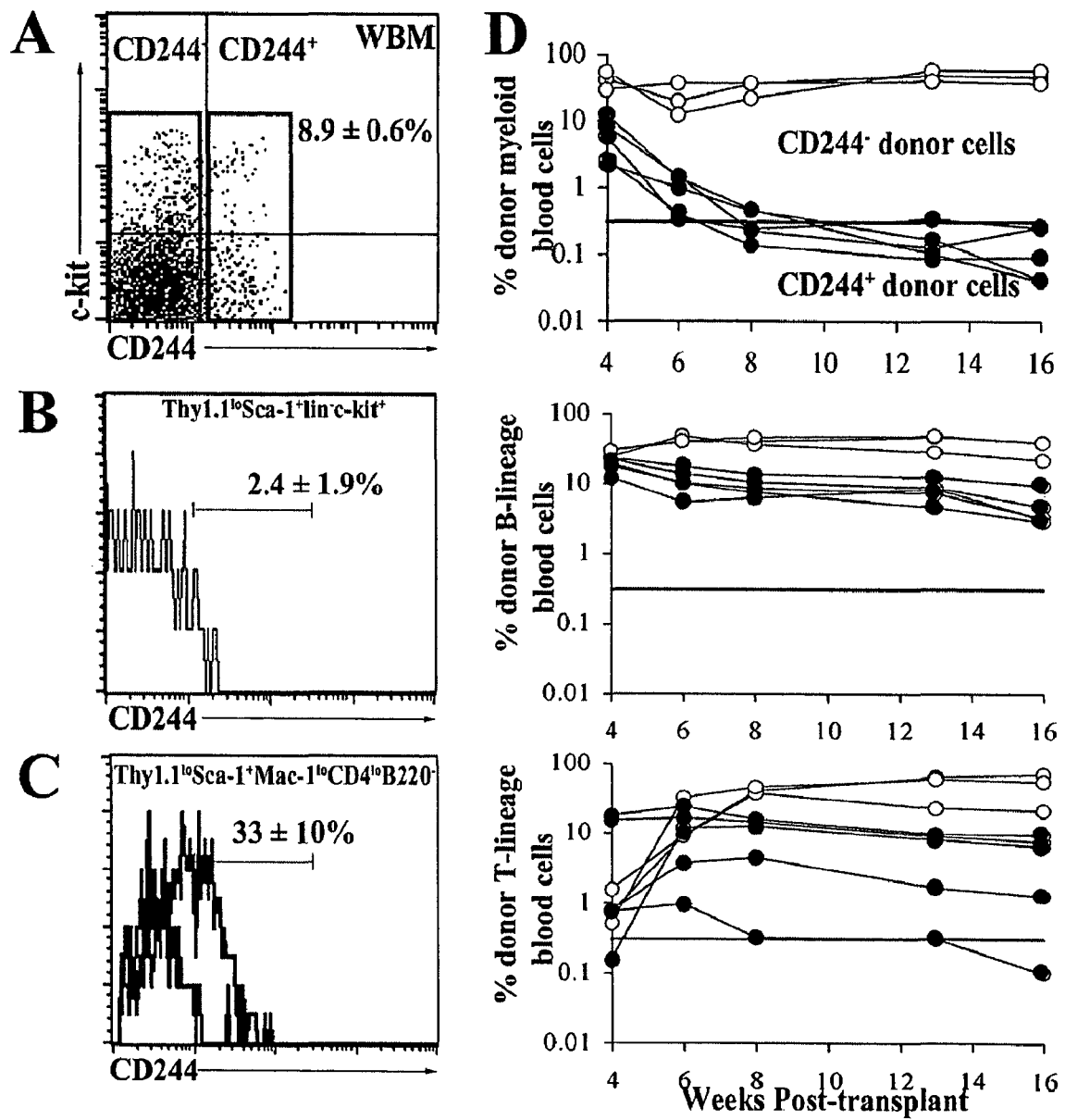
FIG. 2: HSCs are contained within the CD244⁻ population of bone marrow cells while transiently reconstituting multipotent progenitors are contained within the CD244⁺ fraction. CD244 versus c-kit expression shows that only 8.9% of bone marrow cells express CD244 (A). CD244 expression was not detected within the Thy-1$^{low}$Sca-1⁺Lineage⁻c-kit⁺ HSC population (B) but was detected on approximately 33% of cells within the Thy-1$^{low}$Sca-1⁺Mac-1$^{lo}$CD4$^{lo}$B220⁻ MPP population (C). Note that the black histogram represents background fluorescence while the blue histogram represents staining with the directly conjugated anti-CD244 antibody. 20,000 CD244⁺ bone marrow cells gave transient multilineage reconstitution in all recipients (filled circles), while 180,000 CD244⁻ bone marrow cells gave long-term multilineage reconstitution in all recipients (open circles). The data are from one of two independent experiments that gave similar results.

Since multiple SLAM family members are expressed in lymphocytes and they interact to coordinately regulate lymphocyte function, the observation that CD150 was differentially expressed between HSCs and MPPs raised the question of whether other SLAM family members might be differentially expressed between hematopoietic progenitors in a complementary manner. To test this, SLAM family member CD244, which was not detected in HSCs by microarray analysis, was examined. At the protein level, only 8.9±0.6% of bone marrow cells expressed CD244 by flow-cytometry (FIG. 2A). Little or no CD244 staining was detected among Thy-1$^{low}$Sca-1$^+$Lineage$^-$c-kit$^+$ HSCs (FIG. 2B) but 33±10% of cells in the Thy-1$^{low}$Sca-1$^+$Mac-1$^{low}$CD4$^{low}$ MPP population were CD244$^+$ (FIG. 2C).

To functionally test whether CD244$^+$ cells were depleted of HSC activity while retaining transiently reconstituting progenitors, two independent competitive reconstitution assays were performed in which 20,000 donor-type CD244$^+$ cells or 180,000 donor-type CD244$^-$ bone marrow cells were transplanted into lethally irradiated recipients along with a radioprotective dose of 200,000 recipient-type whole bone marrow cells (FIG. 2D). Recipients of the CD244$^-$ cells were consistently long-term multilineage reconstituted by donor cells (8/8 recipients) while recipients of the CD244$^+$ cells were consistently transiently multilineage reconstituted (8/8 recipients). Consistent with this, recipients of CD244$^-$ whole bone marrow cells were consistently able to transfer long-term multilineage donor cell reconstitution to secondary recipients, while recipients of CD244$^+$ cells were never able to transfer donor cell reconstitution to secondary recipients (secondary transfers were performed 16 weeks after transplantation into primary recipients; data not shown). These data indicate that HSCs are contained within the CD244$^-$ fraction, while at least some transiently reconstituting MPPs are contained within the CD244$^+$ fraction of bone marrow cells.

By microarray analysis, the SLAM family member CD48 was expressed at significantly higher levels on CD45$^+$ cells as compared to HSCs or MPPs (fold change>3). By flow-cytometry CD48 protein expression was also reduced on HSCs: 43±3% of whole bone marrow cells were CD48$^+$ (FIG. 3A) while only 23±9% of Thy-1$^{low}$Sca-1$^+$Lineage$^-$c-kit$^+$ cells were CD48$^+$ (FIG. 3B).

Figure 3:
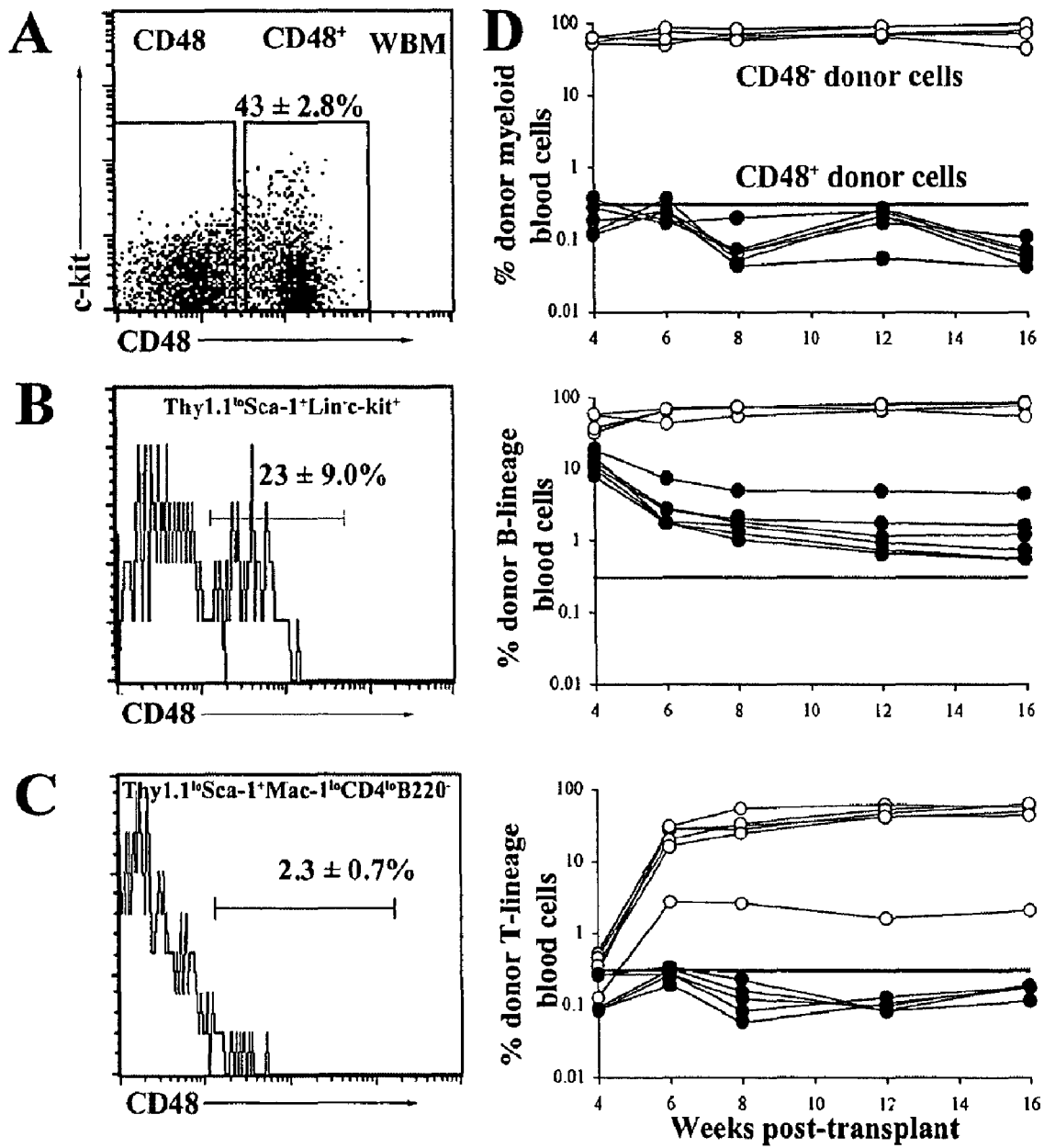
FIG. 3: HSCs and multipotent progenitors are contained within the CD48⁻ but not the CD48⁺ fraction of bone marrow cells. CD48 versus c-kit expression shows that 43% of bone marrow cells express CD48 (A). CD48 expression was detected within the Thy-1$^{low}$Sca-1⁺Lineage⁻c-kit⁺ HSC population (B) but not within the Thy-1$^{low}$Sca-1⁺Mac-1$^{lo}$CD4$^{lo}$B220⁻ MPP population (C). Nonetheless, when the progenitor activity associated with the CD48⁺ and CD48⁻ fractions were measured in competitive reconstitution assays of irradiated mice, all multilineage reconstituting activity was contained within the CD48⁻ cell fraction (D). 80,000 CD48⁺ bone marrow cells gave rise only to B cells in all recipients (filled circles), while 120,000 CD48⁻ bone marrow cells gave long-term multilineage reconstitution in all recipients (open circles). CD48⁻c-kit⁺ cells are highly enriched for primitive progenitor activity but are not visible as a distinct population in panel A because they represent only 0.1% of bone marrow cells.

To functionally test whether CD48$^+$ cells were depleted of HSC activity, we performed competitive reconstitution assays in which 80,000 donor-type CD48$^+$ cells or 120,000 donor-type CD48$^-$ bone marrow cells were transplanted into lethally irradiated recipients along with a radioprotective dose of 200,000 recipient-type whole bone marrow cells (FIG. 3D). Recipients of the CD48$^-$ cells were consistently long-term multilineage reconstituted by donor cells (5/5 recipients) while recipients of the CD48$^+$ cells were consistently reconstituted by B cells (6/6 recipients), but never by myeloid cells (0/6) and rarely by T cells (1/6). These data indicate that HSCs are enriched in the CD48$^-$ fraction and depleted in the CD48$^+$ fraction of bone marrow cells. Although CD48 was not expressed on multipotent progenitors, it was expressed by the majority of progenitors that formed myelocrythroid colonies in culture (data not shown) in addition to early B lineage progenitors (FIG. 3D). Thus, while CD150 was preferentially expressed by HSCs, CD48 was preferentially expressed by restricted hematopoietic progenitors.

Figure 4:
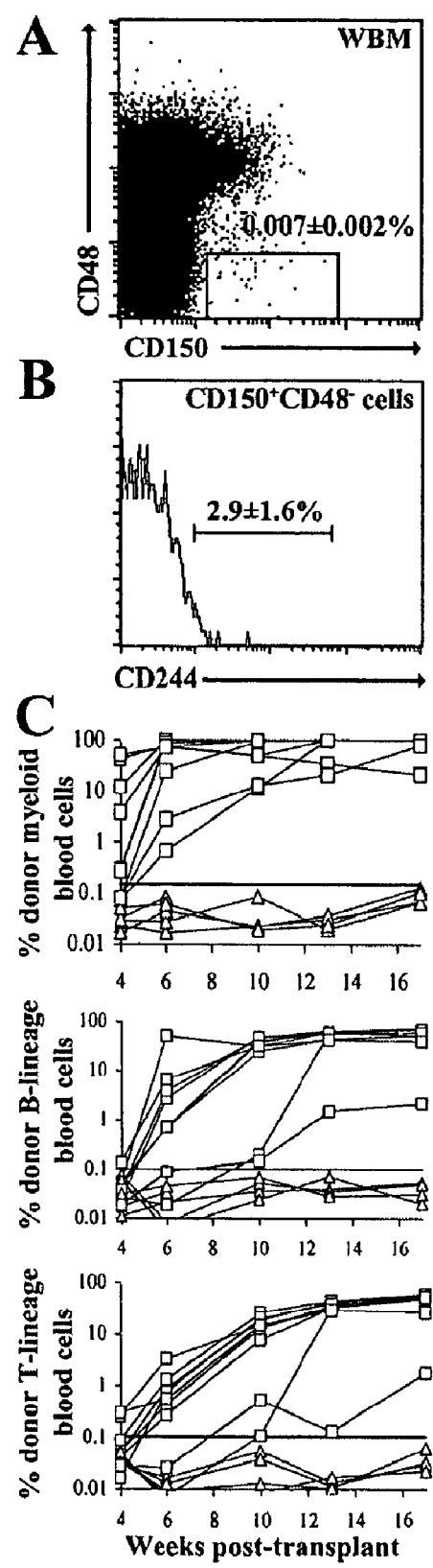
FIG. 4: CD150⁺CD48⁻CD244⁻ cells are rare and highly enriched for long-term reconstituting HSCs. CD150⁺CD48⁻ cells represent only 0.007% of bone marrow cells (A), and these cells were uniformly negative for CD244 expression (B). Injection of 3 donor-type CD150⁺CD48⁻ cells into lethally irradiated recipient mice in a competitive reconstitution assay lead to long-term multilineage reconstitution by donor cells in nine of fourteen mice (open circles) and no reconstitution in five of fourteen mice (open triangles). Each line represents a single recipient mouse.

In the reconstitution assays using single markers, long-term reconstituting HSC activity was contained in the CD150$^+$ but rarely in the CD150$^-$ fraction (FIG. 1D), the CD244$^-$ but not the CD244$^+$ fraction (FIG. 2D), and the CD48$^-$ but not the CD48$^+$ fraction (FIG. 3D). The CD150$^+$CD48$^-$CD244$^-$ fraction of bone marrow cells represented only 0.007±0.002% of whole bone marrow cells, raising the possibility that these cells were very highly enriched for HSC activity. Since CD150$^+$CD48$^-$ cells were uniformly CD244$^-$ (FIG. 4A,B), the reconstituting potential of CD150$^+$CD48$^-$ cells was tested. We performed 3 independent experiments in which 3 or 5 donor-type CD150$^+$CD48$^-$ cells were injected into lethally irradiated recipients, along with a radioprotective dose of recipient-type bone marrow cells (FIG. 4C; Table 3). On average, 1 out of every 3.0±0.5 i.v. injected cells engrafted, and 81±27% of engrafted recipients were long-term multilineage reconstituted. This indicates that by Poisson statistics 1 out of every 4.8±2.7 injected cells engrafted and yielded long-term multilineage reconstitution (Table 3). These results are similar to those obtained with the Thy-1$^{low}$Sca-1$^+$Lineage$^-$c-kit$^+$ cell population (1 in 4.9±2.5; Table 1), which also includes around 0.007% of bone marrow cells, indicating that the simple combination of CD150 and CD48 can nearly uniquely identify HSCs.

TABLE 3

CD150$^+$CD48$^-$ bone marrow cells are highly enriched for long-term self-renewing, multipotent HSCs based on the ability of 3 or 5 CD150$^+$CD48$^-$ cells to competitively reconstitute lethally irradiated mice.

| Cell dose | Mice that engrafted | Frequency of cells that engrafted | Engrafted mice with long-term multilineage reconstitution | Frequency of cells that long-term multilineage reconstituted (HSCs) |
|---|---|---|---|---|
| 5 | 14/15 | 1 in 2.4 | 93% (13/14) | 1 in 3.1 (13/15) |
| 3 | 4/6 | 1 in 3.2 | 50% (2/4) | 1 in 7.9 (2/6) |
| 3 | 9/14 | 1 in 3.4 | 100% (9/9) | 1 in 3.4 (9/14) |
| Mean ± SD | | 1 in 3.0 ± 0.5 | 81 ± 27% | 1 in 4.8 ± 2.7 |

In regard to Table 3, small numbers of CD45.1+donor HSCs isolated using either CD150 and CD48 only (CD150$^+$CD48$^-$ were transplanted into lethally irradiated CD45.2$^+$ recipients along with 200,000 CD45.2$^+$ whole bone marrow cells). The proportion of recipients that showed long-term multilineage reconstitution by donor type cells is shown.

Figure 5:
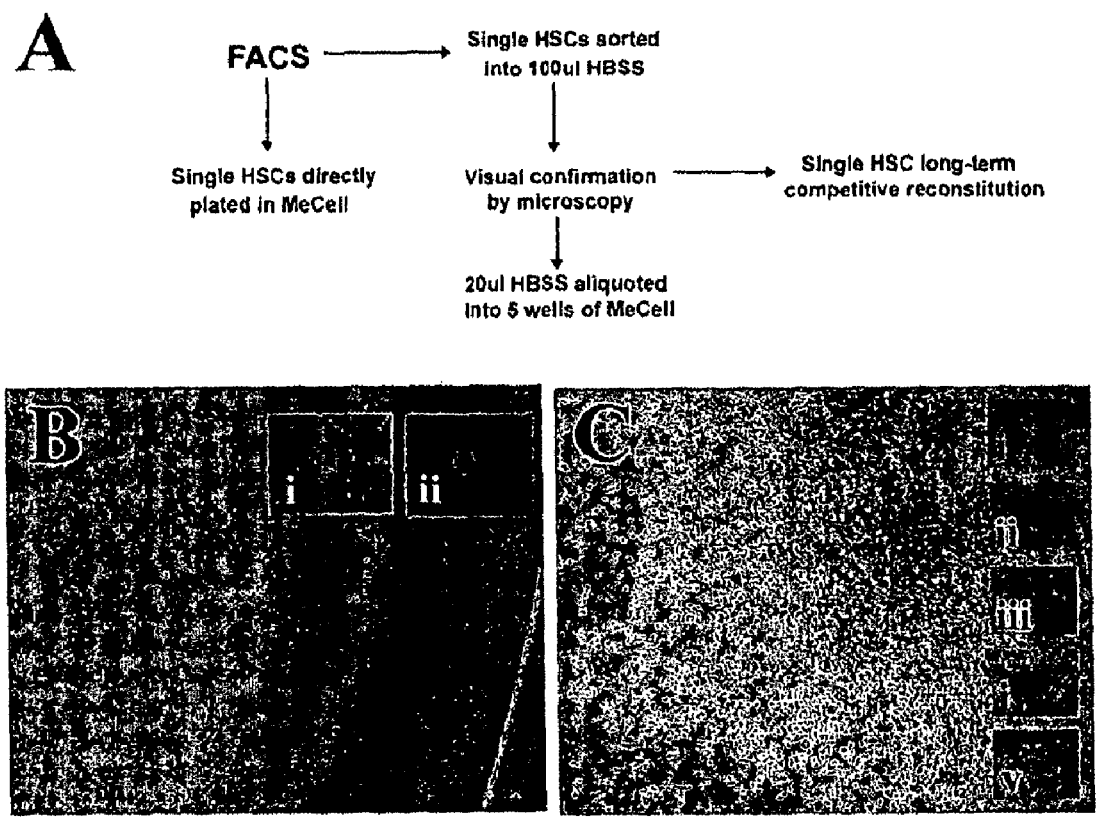
FIG. 5: HSCs at the single cell level are shown to express CD150 and give rise to long-term multi-lineage reconstitution. Single CD150⁺Sca-1⁺Lin⁻CD48⁻c-kit⁺ HSCs were sorted and then resorted by flow-cytometry (FACSVantage SE) on Counter mode using doublet discrimination (A). Single cells were deposited into 100 μl of sterile HBSS buffer containing 2.5 μg/ml Hoechst 33342 (Sigma) and 5.0 μg/ml verapamil (Sigma) in individual wells of a 96-well plate (B). After the presence of a single cell was assessed using light microscopy (i) and confirmed using UV florescence microscopy (ii), the entire contents of each well were injected into lethally irradiated recipients along with a radioprotective dose of 300,000 recipient-type CD150⁻ bone marrow cells in competitive repopulation assays. In none of more than 150 wells visually inspected for the presence of a single cell was more than one cell seen. In control studies to functionally test whether there was only a single cell per well, the contents of each well were divided into five equal volumes and plated onto separate wells of methylcellulose and allowed to form colonies (C). In three separate experiments, when the contents of a well containing a single sorted cell were diluted into five separate wells of methylcellulose, 90.0±10.0% of the sets of five methylcellulose wells contained a single hematopoietic colony and in no circumstance (0/48) was more than one colony observed. When single cells were directly plated into methylcellulose, 93.3±7.6% of single cells formed hematopoictic colonies. There was thus no difference between the clonogenicity of directly plated HSCs or of diluted HSCs (p=0.67). The contents of a representative set of five methylcellulose cultures is shown in the inset (i-v). These results confirm that only a single cell was sorted per well in these experiments and that at the single cell level these individual cells expressed CD150 and were able to give rise to long-term multilineage reconstitution consistent with their characterization as HSCs.

Furthermore, irradiated mice were competitively reconstituted with single CD150$^+$CD48$^-$Sca-1$^+$Lineage$^-$c-kit$^+$ cells in five independent experiments (Table 4). Only 0.003±0.0009% of bone marrow cells were CD150$^+$CD48$^-$Sca-1$^+$Lineage$^-$c-kit$^+$. One CD150$^+$CD48$^-$Sca-1$^+$Lineage$^-$c-kit$^+$ cell was sorted per well and then the contents of each well were individually injected into the recipients. Visual inspection confirmed the presence of a single cell per well prior to injection, and functionally confirmed the presence of a single cell per well in control studies (FIG. 5). On average, 58±10% of recipients were engrafted by donor cells after being injected by a single CD150$^+$CD48$^-$Sca-1$^+$Lineage$^-$c-kit$^+$ cell, and 82±14% of these engrafted recipients exhibited long-term multilineage reconstitution by donor cells. This corresponds to 1 out of every 2.2±0.3 i.v. injected cells engrafting and giving long-term multilineage reconstitution. In contrast, the CD150$^-$ subset of the Thy-1$^{low}$Sca-1$^+$Lineage$^-$c-kit$^+$ population did not give multilineage differentiation when 5 of these cells were injected per irradiated recipient in a competitive reconstitution assay (data not shown). Of the 10 recipients injected with CD150$^-$Thy-1$^{low}$Sca-1$^+$Lineage$^-$c-kit$^+$ cells, most mice showed no donor cell reconstitution. This demonstrates that the combination of markers for CD150 and CD48 with previously identified HSC markers significantly increases HSC purity.

TABLE 4

Competitive reconstitution of irradiated mice with single CD150$^+$CD48$^-$Sca-1$^+$Lineage$^-$ c-kit$^+$ cells revealed that these cells were highly enriched for long-term reconstituting multipotent HSCs.

| Experiment | Mice that engrafted | Frequency of cells that engrafted | Engrafted mice with long-term multilineage reconstitution | Frequency of cells that long-term multilineage reconstituted (HSCs) |
|---|---|---|---|---|
| 1 | 10/15 | 1 in 1.5 | 70% (7/10) | 1 in 2.1 (7/15) |
| 2 | 6/9 | 1 in 1.5 | 66% (4/6) | 1 in 2.3 (4/9) |
| 3 | 8/18 | 1 in 2.3 | 88% (7/8) | 1 in 2.6 (7/18) |
| 4 | 8/15 | 1 in 1.9 | 88% (7/8) | 1 in 2.1 (7/15) |
| 5 | 7/12 | 1 in 1.7 | 100% (7/7) | 1 in 1.7 (7/12) |
| Mean ± SD | 58 ± 10% | 1 in 1.8 ± 0.3 | 82 ± 14% | 1 in 2.2 ± 0.3 |

In regard to Table 4, single $CD150^+CD48^-Sca-1^+Lineage^-$ $c-kit^+$ cells were sorted into different wells of 96 well plates, and the wells were visually inspected to confirm that only a single cell was sorted. Then the contents of each well were individually drawn into different syringes and injected along with a 300,000 recipient type $CD150^-$ bone marrow cells for radioprotection.

Materials and Methods

Description of FACS Sorting of Stem Cell Populations for Functional Assays and Microarray Analysis Cells were flushed from each marrow cavity with Hank's Buffered Salt Solution without calcium or magnesium, supplemented with 2% heat-inactivated calf serum (Gibco, Grand Island N.Y.; $HBSS^+$) using a 3-ml syringe and 27G needle. Cells were triturated into single cell suspension and filtered through nylon screen (45 um, Sefar America, Kansas City Mo.) prior to antibody staining.

Hematopoietic stem cell populations ($Mac-1^-CD4^-c-kit^+$; $Mac-1^{lo}CD4^{lo}$) for identification of CD150 and other SLAM family member expression profiles on HSCs and hematopoietic precursors were isolated as previously described (Morrison et al., 1994 and Morrison et al., 1997, supra). Briefly, whole bone marrow or other hematopoietic tissue cells were incubated with unconjugated monoclonal antibodies to lineage specific surface molecules including B220 (6B2), CD3 (KT31.1), CD5 (53-7.3), CD8 (53-6.7), Gr-1 (8C5) and Ter119. Following dilution, pelleted cells were resuspended in anti-rat IgG specific $F(ab)_2$ fragment conjugated to phycoerythrin (PE; Jackson ImmunoResearch, West Grove Pa.). Cells were subsequently stained with directly conjugated antibodies to Sca-1 (Ly6A/E; allophycocyanin (APC)), c-kit (2B8; biotin), Thy-1.1 (19XE5; fluorescein-5-isothiocyanate (FITC)), Mac-1 (M1/70; PE) and CD4 (GK1.5; PE).

Cells sorted according to expression of CD150 were incubated with unconjugated antibody to CD150 (26D12 received from DNAX, Palo Alto Calif.), and subsequently stained with goat anti-rat IgG specific $F(ab)_2$ fragment conjugated to FITC (Jackson ImmunoResearch) or goat anti-rat IgG (H+L) APC (Jackson ImmunoResearch). Cells sorted according to CD48 expression were stained with directly conjugated CD48 (FITC or PE; Pharmingen, San Jose, Calif.).

Prior to FACS analysis, cells were resuspended in 2 µg/ml 7-AAD (Molecular Probes) to allow for discrimination of viable cells. Only live ($7-AAD^-$) cells were included in every analysis. All antibodies were purchased from BD Pharmingen (San Diego Calif.) unless otherwise noted. All flow-cytometry was performed on a FACS Vantage dual laser flow-cytometer (Becton-Dickinson, San Jose Calif.).

Description of In Vitro and In Vivo Assays Assessing Functional Activity of HSCs Methylcellulose culture was performed as previously described (Morrison et al., 1994). Briefly, unfractionated bone marrow cells, unfractionated splenocytes, or single resorted hematopoietic progenitors were plated in the wells of a 96-well plate (Corning, Corning N.Y.) containing 100 µl 1.0% methylcellulose (Stem Cell Technologies, Vancouver BC). The methylcellulose was supplemented with 20% charcoal absorbed fetal bovine serum (Cocalico, Reamstown, Pa.), 1% BSA (Sigma), 1% penicillin/streptomycin (Gibco) 50 ng/ml stem cell factor (SCF), 10 ng/ml interleukin-3 (IL-3), 10 ng/ml interleukin-6 (IL-6), 3 U/ml erythropoietin (Epo), 10 ng/ml Flt-3 and 10 ng/ml thrombopoietin (Tpo). All cytokines for hematopoietic culture were obtained from R&D Systems (Minneapolis Minn.). Colonies were maintained at 37° C. in fully humidified chambers containing 6% $CO_2$. Colony formation was scored after 10-14 days of culture.

Long-term competitive reconstitution assays were performed as previously described (See, Morrison et al., 1994 and Morrison et al. 1997 supra) with slight modifications. Briefly, greater than 8 week-old CD45.2 recipient animals were lethally irradiated with a Cobalt irradiation source delivering approximately 75 rads/min. The mice received two doses of 550-570rad, delivered at least three hours apart. $CD45.1^+$ stem or progenitor cells were resorted into individual wells of a 96-well plate containing $2-3 \times 10^5$ $CD45.2^+$ whole bone marrow cells in 100 µl $HBSS^+$. The contents of individual wells were drawn into a 500 ml insulin syringe (Becton-Dickinson) and injected into the retro-orbital sinus of lethally irradiated, anesthetized $CD45.2^+$ recipients. Recipients were maintained on antibiotic water (1.1 g neomycin sulfate and $10^6$ U/L polymixin B sulfate; Sigma) ad libitum. After 4, 6, 8, 12 and 16 weeks post transplant, peripheral blood was obtained from the tail veins of individual recipients, subject to ammonium-chloride red cell lysis, and stained with antibodies to CD45.1 (104) directly conjugated to FITC, and B220 (6B2), Mac-1 (M1/70), CD3 (KT31.1) and Gr-1 (8C5) directly conjugated to PE or APC as described (Morrison et al., 1994 and Morrison et al., 1997).

Description of cDNA Production, Amplification Microarray Hybridization and Confirmation by Quantitative PCR Demonstrating Expression of CD150 by HSCs at the RNA Level Total RNA was extracted from 5,000 freshly isolated LTSR or NSR using Trizol with 250 µg/ml glycogen (Roche Diagnostic Corporation, Indianapolis, Ind.). RNA was extracted following the manufacturer's instructions. The extracted RNA (30 µl volume) was treated for 20 minutes at 37° C. with 2 µl of RNase-free DNaseI (2 U/µl; Ambion, Austin, Tex.) in the presence of 2 µl of RNase inhibitor (10U/µl) (Invitrogen). The RNA was then purified with RNeasy Mini Kit (Qiagen, Valencia Calif.) according to the manufacturer's instructions and washed 3 times with 500 µl of RNase-free water in a Microcon YM-100 (Millipore, Bedford Mass.). After adding 0.025 µg $T7-d(T)_{24}$ primer (containing a T7 RNA polymerase binding sequence; 5'-GGCCAGTGAATTGTAATACGACT-CACTATAGGGAGGCGG(T)24 (SEQ ID NO:1); Proligo, Boulder Colo.), the RNA was dried down to 2.5 µl. RNA was amplified through two consecutive rounds of amplification using a modified version of the method of Baugh et al., Nucleic Acids Res., 29, E29, 2001. To make cDNA, first strand was synthesized using $T7-d(T)_{24}$ primer. After second strand synthesis, complementary RNA (cRNA) was generated by T7 RNA polymerase (Promega, Madison Wis.). For the second round of amplification, first strand cDNA was synthesized using random hexamers and second strand was synthesized using the $T7-d(T)_{24}$ primer. The double stranded cDNA was resuspended with 22 µl RNase-free water and transcribed to cRNA with the biotin labeling kit (BioArray Highyleld RNA transcript labeling kit (T7), Enzo Diagnostics, Farmingdale N.Y.) for twelve hours. cRNA was purified using the RNeasy Mini Kit. Around 60 µg of biotinylated cRNA were obtained from two rounds of RNA amplification from 5,000 HSCs.

After fragmentation, 15 μg of HSC cRNA were hybridized per chip to Mouse Genome U74 Arrays (Chips A, B and C; AFFYMETRIX). The chips were hybridized and scanned according to the manufacturer's instructions. Signal intensities were read and analyzed using methods described previously (Iwashita et al., Science 2003; 301:972, herein incorporated by reference). To measure fold changes, all negative signal intensity values or values less than 100 were set to 100. To calculate the squared Pearson's correlation coefficient ($R^2$) between two groups, we transformed each value to the base 10 logarithm ($\log_{10}$). $\log_{10}$ transformation is required because the Pearson's correlation coefficient is designed to be calculated based on normally distributed data, and the untransformed data are not normally distributed. The statistical significance of differences in signal intensity for each probe set were evaluated by student's T-test using the $\log_{10}$ transformed values from 3 independent replicates per cell type.

2,000 to 10,000 Mac-1$^-$CD4$^-$c-kit$^+$ HSCs, Mac-1$^{lo}$CD4$^{lo}$B220$^{+/-}$ MPPs or CD45$^+$ WBM cells were directly sorted into 400 μl Trizol (Ambion, Austin Tex.) containing 250 μg/ml glycogen (Roche, Indianapolis Ind.). RNA was extracted according to manufacturer's instructions. The extracted RNA (30 μl volume) was treated for 20 minutes at 37° C. with 2 μl RNase-free DNase-1 (2 U/μl; Ambion) in the presence of 2 μl RNase inhibitor (10 U/μl; Invitrogen). The RNA was then purified using an RNeasy Mini Kit (Qiagen, Valencia Calif.) according to manufacturer's instructions and washed three times with 500 μl RNase-free water. The RNA was used for making cDNA by reverse transcription with 1 μg random hexamer. The cDNA was extracted with phenol-chloroform and precipitated with 20 μg glycogen. After dissolving the cDNA with RNase-free water, cDNA equivalent to 200 cells was used for each PCR reaction. qRT-PCR was performed in triplicate using three independent cell samples. Primers were designed to have a Tm of ~59° C. and to generate short amplicons (100-150 bp). The PCR reactions were performed using a LightCycler (Roche Diagnostic Corporation, Indianapolis Ind.) according to the manufacturer's instructions. The RNA content of samples compared by qRT-PCR was normalized based on the amplification of hypozanthine phosphribosyl transferase (HPRT). In addition to confirming the specificity of the qRT-PCR reactions by examining the melting curves of the products, qRT-PCR products were separated in 2% agarose gels to confirm the presence of a single band of the expected size. To estimate the magnitude of the difference in the expression levels of individual RNAs between samples, we assumed that one cycle difference in the timing of amplification by qRT-PCR was equivalent to a 1.8-fold difference in expression level.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cell biology or related fields are intended to be within the scope of the following claims.

We claim:

1. A purified cell sample, wherein said purified cell sample comprises cells, and wherein at least 50% of said cells in said purified cell sample are CD150$^+$CD48$^-$ and are HSCs that are able to provide long-term multi-lineage reconstitution.

2. The purified cell sample of claim 1, wherein said CD150$^+$CD48$^-$ HSCs are bone marrow HSCs.

3. The purified cell sample of claim 1, wherein said CD150$^+$CD48$^-$ HSCs are fetal liver HSCs.

4. The purified cell sample of claim 1, wherein said CD150$^+$CD48$^-$ HSCs are adult spleen HSCs.

5. The purified cell sample of claim 1, wherein said CD150$^+$CD48$^-$ HSCs are umbilical cord HSCs.

6. The purified cell sample of claim 1, wherein said CD150$^+$CD48$^-$ HSCs are peripheral blood HSCs.

7. A purified cell sample, wherein said purified cell sample comprises cells, and wherein at least 75% of said cells in said purified cell sample are CD150$^+$CD48$^-$ and are HSCs that are able to provide long-term multi-lineage reconstitution.

8. The purified cell sample of claim 7, wherein said CD150$^+$CD48$^-$ HSCs are bone marrow HSCs.

9. The purified cell sample of claim 7, wherein said CD150$^+$CD48$^-$ HSCs are fetal liver HSCs.

10. The purified cell sample of claim 7, wherein said CD150$^+$CD48$^-$ HSCs are adult spleen HSCs.

11. The purified cell sample of claim 7, wherein said CD150$^+$CD48$^-$ HSCs are umbilical cord HSCs.

12. The purified cell sample of claim 7, wherein said CD150$^+$CD48$^-$ HSCs are peripheral blood HSCs.

* * * * *

SEQUENCE LISTING

```
<160> NUMBER OF SEQ ID NOS: 1

<210> SEQ ID NO 1
<211> LENGTH: 63
<212> TYPE: DNA
<213> ORGANISM: Artificial Sequence
<220> FEATURE:
<223> OTHER INFORMATION: Synthetic

<400> SEQUENCE: 1
ggccagtgaa ttgtaatacg actcactata gggaggcggt tttttttttt tttttttttt    60
ttt                                                                  63
```